US007982011B2

(12) United States Patent
Pastan et al.

(10) Patent No.: US 7,982,011 B2
(45) Date of Patent: Jul. 19, 2011

(54) MUTATED ANTI-CD22 ANTIBODIES AND IMMUNOCONJUGATES

(75) Inventors: Ira H. Pastan, Potomac, MD (US); Mitchell Ho, North Potomac, MD (US); Sookhee Bang, Glendale, CA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 716 days.

(21) Appl. No.: 10/580,635

(22) PCT Filed: Nov. 24, 2004

(86) PCT No.: PCT/US2004/039617

§ 371 (c)(1),
(2), (4) Date: Apr. 11, 2007

(87) PCT Pub. No.: WO2005/052006

PCT Pub. Date: Jun. 9, 2005

(65) Prior Publication Data

US 2007/0189962 A1 Aug. 16, 2007

Related U.S. Application Data

(60) Provisional application No. 60/525,371, filed on Nov. 25, 2003.

(51) Int. Cl.

| | |
|---|---|
| ***C12P 21/08*** | (2006.01) |
| ***C07K 16/00*** | (2006.01) |
| ***A61K 39/40*** | (2006.01) |
| ***A61K 39/395*** | (2006.01) |
| ***G01N 33/53*** | (2006.01) |
| ***G01N 33/567*** | (2006.01) |
| ***G01N 33/574*** | (2006.01) |
| ***G01N 33/555*** | (2006.01) |
| *C07K 17/00* | (2006.01) |

(52) U.S. Cl. ............... 530/387.1; 530/387.3; 530/388.1; 530/388.22; 530/388.7; 530/391.1; 530/391.3; 424/130.1; 424/133.1; 424/134.1; 424/138.1; 424/141.1; 424/143.1; 424/152.1; 424/153.1; 424/156.1; 424/178.1; 424/7.1; 424/7.2; 424/7.21; 424/7.23; 424/7.24

(58) Field of Classification Search ........................ None
See application file for complete search history.

(56) References Cited

U.S. PATENT DOCUMENTS

| | | | | |
|---|---|---|---|---|
| 4,892,827 | A * | 1/1990 | Pastan et al. | 435/193 |
| 5,602,095 | A * | 2/1997 | Pastan et al. | 514/12 |
| 5,608,039 | A * | 3/1997 | Pastan et al. | 530/387.3 |

FOREIGN PATENT DOCUMENTS

| | | |
|---|---|---|
| WO | WO 00/73346 A1 | 12/2000 |
| WO | WO 03/027135 A2 | 4/2003 |

OTHER PUBLICATIONS

Mansfield et al. Blood. (1997) 90:2020-2026).*
Pai et al. PNAS (1991) 88:3358-3362.*
Kondo et al. JBC (1988) 263:9470-9475.*
Debinski et al. Bioconj. Chem. (1994) 5:40-46.*
Exhibit A. PubMed Search PE40. Aug. 26, 2010. pp. 1-20.*
Exhibit B. PubMed Search PE38. Aug. 26, 2010. pp. 1-21.*
Exhibit C. PubMed Search PE38QQR. Aug. 26, 2010. pp. 1-7.*
Exhibit D. PubMed Search PE38KDEL. Aug. 26, 2010. pp. 1-10.*
Exhibit E. PubMed Search PE4E. Aug. 26, 2010. pp. 1-3.*
Exhibit F. PubMed Search PE35. Aug. 26, 2010. pp. 1-20.*
Exhibit G. Aug. 26, 2010. pp. 1-39.*
Bang, Sookhee et al.; "HA22 (R490A) is a recombinant immunotoxin with increased antitumor activity and therapeutic index"; 2004, *Proceedings of the American Association for Cancer Research Annual Meeting*, vol. 45, p. 144.
Bang, Sookhee et al.; "HA22 (R490A) is a Recombinant Immunotoxin with Increased Antitumor Activity without an Increase in Animal Toxicity"; 2005, *Clinical Cancer Research* vol. 2, pp. 1545-1550.
Beers, Richard et al.; "Immunotoxins with Increased Activity against Epidermal Growth Factor Receptor vIII-expressing Cells Produced by Antibody Phage display"; 2000, *Clinical Cancer Research* vol. 6 pp. 2835-2843.
Brinkmann, Ulrich et al.; "Alteration of a protease-sensitive region of Pseudomonas exotoxin prolongs its survival in the circulation of mice"; 1992 *Proceedings of the National Academy of Science*, vol. 89, pp. 3065-3069.
Chowdhury, Partha S. et al.; "Improving antibody affinity by mimicking somatic hypermutation in vitro"; 1999, *Nature Biotechnology*, vol. 17, pp. 568-572.
Decker, Thomas et al.; "Induction of Caspase-Dependent Programmed Cell Death in B-CLL Cells by Recombinant Anti-CD22 Immunotoxins"; 2003, *Blood*, vol. 102, No. 11, p. 439a.
Ho, Mitchell et al.; "In Vitro Antibody Evolution Targeting Germline Hot Spots to Increase Activity of an Anti-CD22 Immunotoxin"; 2005, *The Journal of Biological Chemistry*, vol. 280, No. 1, pp. 607-617.

(Continued)

*Primary Examiner* — Chun Dahle
(74) *Attorney, Agent, or Firm* — Kilpatrick Townsend & Stockton LLP

(57) ABSTRACT

Recombinant immunotoxins are fusion proteins composed of the Fv domains of antibodies fused to bacterial or plant toxins. RFB4 (Fv)-PE38 is an immunotoxin that targets CD22 expressed on B cells and B cell malignancies. The present invention provides antibodies and antibody fragments that have improved ability to bind the CD22 antigen compared to RFB4. Immunotoxins made with the antibodies and antibody fragments of the invention have improved cytotoxicity to CD22-expressing cancer cells. Compositions that incorporate these antibodies into chimeric immunotoxin molecules that can be used in medicaments and methods for inhibiting the growth and proliferation of such cancers. Additionally, the invention provides a method of increasing the cytotoxicity of forms of *Pseudomonas* exotoxin A ("PE") with the mutation of a single amino acid, as well as compositions of such mutated PEs, nucleic acids encoding them, and methods for using the mutated PEs.

40 Claims, 8 Drawing Sheets

OTHER PUBLICATIONS

Kreitman, Robert J.; "Chimeric fusion proteins—*Pseudomonas* exotoxin-based"; 2001, *Current Opinion in Investigational Drugs*, vol. 2, No. 9, pp. 1282-1293.

Salvatore, Giuliana et al.; "Improved Cytotoxic Activity toward Cell Lines and Fresh Leukemia Cells of a Mutant Anti-CD22 Immunotoxin Obtained by Antibody Phage Display"; 2002, *Clinical Cancer Research*, vol. 8, pp. 995-1002.

Tsutsumi, Yasuo et al.; "Site-specific chemical modification with polyethylene glycol of recombinant immunotoxin anti-Tac(Fv)-PE38 (LMB-2) improves antitumor activity and reduces animal toxicity and immunogenicity"; 2000, *Proceedings of the National Academy of Science*, vol. 97, No. 15, pp. 8548-8553.

Yates, Susan P. et al.; "A Catalytic Loop within Pseudomonas aeruginosa Exotoxin A Modulates Its Transferase Activity"; 2001, *The Journal of Biological Chemistry*, vol. 276, No. 37, pp. 35029-35036.

* cited by examiner

VL

```
D I Q M T Q T T S S L S A S L G D R V T
gatatccagatgacccagactacatcctccctgtctgcctctctgggagacagagtcacc
I S C R A S Q D I S N Y L N W Y Q Q K P
attagttgcagggcaagtcaggacattagcaattatttaaactggtatcagcagaaacca
D G T V K L L I Y Y T S I L H S G V P S
gatggaactgttaaactcctgatctactacacatcaatattacactcaggagtcccatca
R F S G S G S G T D Y S L T I S N L E Q
aggttcagtggcagtgggtctggaacagattattctctcaccattagcaacctggagcaa
E D F A T Y F C Q Q G N T L P W T F G G
gaagattttgccacttacttttgccaacagggtaatacgcttccgtggacgttcggtgga
G T K L E I K
ggcaccaagctggaaatcaaa
```

VH

```
E V Q L V E S G G G L V K P G G S L K L
gaagtgcagctggtggagtctgggggaggcttagtgaagcctggagggtccctgaaactc
S C A A S G F A F S I Y D M S W V R Q T
tcctgtgcagcctctggattcgctttcagtatctatgacatgtcttgggttcgccagact
P E K R L E W V A Y I S S G G G T T Y Y
ccggagaagaggctggagtgggtcgcatacattagtagtggtggtggtaccacctactat
P D T V K G R F T I S R D N A K N T L Y
ccagacactgtgaagggccgattcaccatctccagagacaatgccaagaacaccctgtac
L Q M S S L K S E D T A M Y Y C A R H S
ctgcaaatgagcagtctgaagtctgaggacacagccatgtattactgtgcaagacatagt
G Y G S S Y G V L F A Y W G Q G T L V T
ggctacggtagtagctacggggttttgtttgcttactggggccaagggactctggtcact
V S A
gtctctgca
```

FIG. 1

*Nucleotide/residue numbering shown first followed by Kabat Numbering*

| | | | | |
|---|---|---|---|---|
| 1 | 0 | --- | --- | - |
| 2 | 1 | gat | ASP | D |
| 3 | 2 | atc | ILE | I |
| 4 | 3 | cag | GLN | Q |
| 5 | 4 | atg | MET | M |
| 6 | 5 | acc | THR | T |
| 7 | 6 | cag | GLN | Q |
| 8 | 7 | act | THR | T |
| 9 | 8 | aca | THR | T |
| 10 | 9 | tcc | SER | S |
| 11 | 10 | tcc | SER | S |
| 12 | 11 | ctg | LEU | L |
| 13 | 12 | tct | SER | S |
| 14 | 13 | gcc | ALA | A |
| 15 | 14 | tct | SER | S |
| 16 | 15 | ctg | LEU | L |
| 17 | 16 | gga | GLY | G |
| 18 | 17 | gac | ASP | D |
| 19 | 18 | aga | ARG | R |
| 20 | 19 | gtc | VAL | V |
| 21 | 20 | acc | THR | T |
| 22 | 21 | att | ILE | I |
| 23 | 22 | agt | SER | S |
| 24 | 23 | tgc | CYS | C |
| 25 | 24 | agg | ARG | R |
| 26 | 25 | gca | ALA | A |
| 27 | 26 | agt | SER | S |
| 28 | 27 | cag | GLN | Q |
| 29 | 27A | --- | --- | - |
| 30 | 27B | --- | --- | - |
| 31 | 27C | --- | --- | - |
| 32 | 27D | --- | --- | - |
| 33 | 27E | --- | --- | - |
| 34 | 27F | --- | --- | - |
| 35 | 28 | gac | ASP | D |
| 36 | 29 | att | ILE | I |
| 37 | 30 | agc | SER | S |
| 38 | 31 | aat | ASN | N |
| 39 | 32 | tat | TYR | Y |
| 40 | 33 | tta | LEU | L |
| 41 | 34 | aac | ASN | N |
| 42 | 35 | tgg | TRP | W |
| 43 | 36 | tat | TYR | Y |
| 44 | 37 | cag | GLN | Q |
| 45 | 38 | cag | GLN | Q |
| 46 | 39 | aaa | LYS | K |
| 47 | 40 | cca | PRO | P |
| 48 | 41 | gat | ASP | D |
| 49 | 42 | gga | GLY | G |
| 50 | 43 | act | THR | T |
| 51 | 44 | gtt | VAL | V |
| 52 | 45 | aaa | LYS | K |
| 53 | 46 | ctc | LEU | L |
| 54 | 47 | ctg | LEU | L |
| 55 | 48 | atc | ILE | I |
| 56 | 49 | tac | TYR | Y |
| 57 | 50 | tac | TYR | Y |
| 58 | 51 | aca | THR | T |
| 59 | 52 | tca | SER | S |
| 60 | 53 | ata | ILE | I |
| 61 | 54 | tta | LEU | L |
| 62 | 55 | cac | HIS | H |
| 63 | 56 | tca | SER | S |
| 64 | 57 | gga | GLY | G |
| 65 | 58 | gtc | VAL | V |
| 66 | 59 | cca | PRO | P |
| 67 | 60 | tca | SER | S |
| 68 | 61 | agg | ARG | R |
| 69 | 62 | ttc | PHE | F |
| 70 | 63 | agt | SER | S |
| 71 | 64 | ggc | GLY | G |
| 72 | 65 | agt | SER | S |
| 73 | 66 | ggg | GLY | G |
| 74 | 67 | tct | SER | S |
| 75 | 68 | gga | GLY | G |
| 76 | 69 | aca | THR | T |
| 77 | 70 | gat | ASP | D |
| 78 | 71 | tat | TYR | Y |
| 79 | 72 | tct | SER | S |
| 80 | 73 | ctc | LEU | L |
| 81 | 74 | acc | THR | T |
| 82 | 75 | att | ILE | I |
| 83 | 76 | agc | SER | S |
| 84 | 77 | aac | ASN | N |
| 85 | 78 | ctg | LEU | L |
| 86 | 79 | gag | GLU | E |
| 87 | 80 | caa | GLN | Q |
| 88 | 81 | gaa | GLU | E |
| 89 | 82 | gat | ASP | D |
| 90 | 83 | ttt | PHE | F |
| 91 | 84 | gcc | ALA | A |
| 92 | 85 | act | THR | T |
| 93 | 86 | tac | TYR | Y |
| 94 | 87 | ttt | PHE | F |
| 95 | 88 | tgc | CYS | C |
| 96 | 89 | caa | GLN | Q |
| 97 | 90 | cag | GLN | Q |
| 98 | 91 | ggt | GLY | G |
| 99 | 92 | aat | ASN | N |
| 100 | 93 | acg | THR | T |
| 101 | 94 | ctt | LEU | L |
| 102 | 95 | ccg | PRO | P |
| 103 | 95A | --- | --- | - |
| 104 | 95B | --- | --- | - |
| 105 | 95C | --- | --- | - |
| 106 | 95D | --- | --- | - |
| 107 | 95E | --- | --- | - |
| 108 | 95F | --- | --- | - |
| 109 | 96 | tgg | TRP | W |
| 110 | 97 | acg | THR | T |
| 111 | 98 | ttc | PHE | F |
| 112 | 99 | ggt | GLY | G |
| 113 | 100 | gga | GLY | G |
| 114 | 101 | ggc | GLY | G |
| 115 | 102 | acc | THR | T |
| 116 | 103 | aag | LYS | K |
| 117 | 104 | ctg | LEU | L |
| 118 | 105 | gaa | GLU | E |
| 119 | 106 | atc | ILE | I |
| 120 | 106A | --- | --- | - |
| 121 | 107 | aaa | LYS | K |
| 122 | 108 | | | |
| 123 | 109 | | | |

*FIG. 2*

*Nucleotide/residue numbering shown first followed by Kabat Numbering*

| | | | | |
|---|---|---|---|---|
| 1 | 0 | --- | --- | - |
| 2 | 1 | gaa | GLU | E |
| 3 | 2 | gtg | VAL | V |
| 4 | 3 | cag | GLN | Q |
| 5 | 4 | ctg | LEU | L |
| 6 | 5 | gtg | VAL | V |
| 7 | 6 | gag | GLU | E |
| 8 | 7 | tct | SER | S |
| 9 | 8 | ggg | GLY | G |
| 10 | 9 | gga | GLY | G |
| 11 | 10 | ggc | GLY | G |
| 12 | 11 | tta | LEU | L |
| 13 | 12 | gtg | VAL | V |
| 14 | 13 | aag | LYS | K |
| 15 | 14 | cct | PRO | P |
| 16 | 15 | gga | GLY | G |
| 17 | 16 | ggg | GLY | G |
| 18 | 17 | tcc | SER | S |
| 19 | 18 | ctg | LEU | L |
| 20 | 19 | aaa | LYS | K |
| 21 | 20 | ctc | LEU | L |
| 22 | 21 | tcc | SER | S |
| 23 | 22 | tgt | CYS | C |
| 24 | 23 | gca | ALA | A |
| 25 | 24 | gcc | ALA | A |
| 26 | 25 | tct | SER | S |
| 27 | 26 | gga | GLY | G |
| 28 | 27 | ttc | PHE | F |
| 29 | 28 | gct | ALA | A |
| 30 | 29 | ttc | PHE | F |
| 31 | 30 | agt | SER | S |
| 32 | 31 | atc | ILE | I |
| 33 | 32 | tat | TYR | Y |
| 34 | 33 | gac | ASP | D |
| 35 | 34 | atg | MET | M |
| 36 | 35 | tct | SER | S |
| 37 | 35A | --- | --- | - |
| 38 | 35B | --- | --- | - |
| 39 | 36 | tgg | TRP | W |
| 40 | 37 | gtt | VAL | V |
| 41 | 38 | cgc | ARG | R |
| 42 | 39 | cag | GLN | Q |
| 43 | 40 | act | THR | T |
| 44 | 41 | ccg | PRO | P |
| 45 | 42 | gag | GLU | E |
| 46 | 43 | aag | LYS | K |
| 47 | 44 | agg | ARG | R |
| 48 | 45 | ctg | LEU | L |
| 49 | 46 | gag | GLU | E |
| 50 | 47 | tgg | TRP | W |
| 51 | 48 | gtc | VAL | V |
| 52 | 49 | gca | ALA | A |
| 53 | 50 | tac | TYR | Y |
| 54 | 51 | att | ILE | I |
| 55 | 52 | agt | SER | S |
| 56 | 52A | agt | SER | S |
| 57 | 52B | --- | --- | - |
| 58 | 52C | --- | --- | - |
| 59 | 53 | ggt | GLY | G |
| 60 | 54 | ggt | GLY | G |
| 61 | 55 | ggt | GLY | G |
| 62 | 56 | acc | THR | T |
| 63 | 57 | acc | THR | T |
| 64 | 58 | tac | TYR | Y |
| 65 | 59 | tat | TYR | Y |
| 66 | 60 | cca | PRO | P |
| 67 | 61 | gac | ASP | D |
| 68 | 62 | act | THR | T |
| 69 | 63 | gtg | VAL | V |
| 70 | 64 | aag | LYS | K |
| 71 | 65 | ggc | GLY | G |
| 72 | 66 | cga | ARG | R |
| 73 | 67 | ttc | PHE | F |
| 74 | 68 | acc | THR | T |
| 75 | 69 | atc | ILE | I |
| 76 | 70 | tcc | SER | S |
| 77 | 71 | aga | ARG | R |
| 78 | 72 | gac | ASP | D |
| 79 | 73 | aat | ASN | N |
| 80 | 74 | gcc | ALA | A |
| 81 | 75 | aag | LYS | K |
| 82 | 76 | aac | ASN | N |
| 83 | 77 | acc | THR | T |
| 84 | 78 | ctg | LEU | L |
| 85 | 79 | tac | TYR | Y |
| 86 | 80 | ctg | LEU | L |
| 87 | 81 | caa | GLN | Q |
| 88 | 82 | atg | MET | M |
| 89 | 82A | agc | SER | S |
| 90 | 82B | agt | SER | S |
| 91 | 82C | ctg | LEU | L |
| 92 | 83 | aag | LYS | K |
| 93 | 84 | tct | SER | S |
| 94 | 85 | gag | GLU | E |
| 95 | 86 | gac | ASP | D |
| 96 | 87 | aca | THR | T |
| 97 | 88 | gcc | ALA | A |
| 98 | 89 | atg | MET | M |
| 99 | 90 | tat | TYR | Y |
| 100 | 91 | tac | TYR | Y |
| 101 | 92 | tgt | CYS | C |
| 102 | 93 | gca | ALA | A |
| 103 | 94 | aga | ARG | R |
| 104 | 95 | cat | HIS | H |
| 105 | 96 | agt | SER | S |
| 106 | 97 | ggc | GLY | G |
| 107 | 98 | tac | TYR | Y |
| 108 | 99 | ggt | GLY | G |
| 109 | 100 | agt | SER | S |
| 110 | 100A | agc | SER | S |
| 111 | 100B | tac | TYR | Y |
| 112 | 100C | ggg | GLY | G |
| 113 | 100D | gtt | VAL | V |
| 114 | 100E | ttg | LEU | L |
| 115 | 100F | --- | --- | - |
| 116 | 100G | --- | --- | - |
| 117 | 100H | --- | --- | - |
| 118 | 100I | --- | --- | - |
| 119 | 100J | --- | --- | - |
| 120 | 100K | ttt | PHE | F |
| 121 | 101 | gct | ALA | A |
| 122 | 102 | tac | TYR | Y |
| 123 | 103 | tgg | TRP | W |
| 124 | 104 | ggc | GLY | G |
| 125 | 105 | caa | GLN | Q |
| 126 | 106 | ggg | GLY | G |
| 127 | 107 | act | THR | T |
| 128 | 108 | ctg | LEU | L |
| 129 | 109 | gtc | VAL | V |
| 130 | 110 | act | THR | T |
| 131 | 111 | gtc | VAL | V |
| 132 | 112 | tct | SER | S |
| 133 | 113 | gca | ALA | A |

*FIG. 3*

SEQUENCE LISTING

<160> NUMBER OF SEQ ID NOS: 30

<210> SEQ ID NO 1
<211> LENGTH: 321
<212> TYPE: DNA
<213> ORGANISM: Mus sp.
<220> FEATURE:
<223> OTHER INFORMATION: RFB4 mouse IgG1 anti-human CD22 monoclonal antibody light chain variable region (VL)
<220> FEATURE:
<221> NAME/KEY: CDS
<222> LOCATION: (1)..(321)
<223> OTHER INFORMATION: RFB4 mouse IgG1 anti-human CD22 monoclonal antibody light chain variable region (VL)

<400> SEQUENCE: 1

```
gat atc cag atg acc cag act aca tcc tcc ctg tct gcc tct ctg gga       48
Asp Ile Gln Met Thr Gln Thr Thr Ser Ser Leu Ser Ala Ser Leu Gly
  1               5                  10                  15

gac aga gtc acc att agt tgc agg gca agt cag gac att agc aat tat       96
Asp Arg Val Thr Ile Ser Cys Arg Ala Ser Gln Asp Ile Ser Asn Tyr
             20                  25                  30

tta aac tgg tat cag cag aaa cca gat gga act gtt aaa ctc ctg atc      144
Leu Asn Trp Tyr Gln Gln Lys Pro Asp Gly Thr Val Lys Leu Leu Ile
         35                  40                  45

tac tac aca tca ata tta cac tca gga gtc cca tca agg ttc agt ggc      192
Tyr Tyr Thr Ser Ile Leu His Ser Gly Val Pro Ser Arg Phe Ser Gly
     50                  55                  60

agt ggg tct gga aca gat tat tct ctc acc att agc aac ctg gag caa      240
Ser Gly Ser Gly Thr Asp Tyr Ser Leu Thr Ile Ser Asn Leu Glu Gln
 65                  70                  75                  80

gaa gat ttt gcc act tac ttt tgc caa cag ggt aat acg ctt ccg tgg      288
Glu Asp Phe Ala Thr Tyr Phe Cys Gln Gln Gly Asn Thr Leu Pro Trp
                 85                  90                  95

acg ttc ggt gga ggc acc aag ctg gaa atc aaa                          321
Thr Phe Gly Gly Gly Thr Lys Leu Glu Ile Lys
            100                 105
```

<210> SEQ ID NO 2
<211> LENGTH: 107
<212> TYPE: PRT
<213> ORGANISM: Mus sp.
<220> FEATURE:
<223> OTHER INFORMATION: RFB4 mouse IgG1 anti-human CD22 monoclonal antibody light chain variable region (VL)

<400> SEQUENCE: 2

```
Asp Ile Gln Met Thr Gln Thr Thr Ser Ser Leu Ser Ala Ser Leu Gly
  1               5                  10                  15

Asp Arg Val Thr Ile Ser Cys Arg Ala Ser Gln Asp Ile Ser Asn Tyr
             20                  25                  30

Leu Asn Trp Tyr Gln Gln Lys Pro Asp Gly Thr Val Lys Leu Leu Ile
         35                  40                  45

Tyr Tyr Thr Ser Ile Leu His Ser Gly Val Pro Ser Arg Phe Ser Gly
     50                  55                  60

Ser Gly Ser Gly Thr Asp Tyr Ser Leu Thr Ile Ser Asn Leu Glu Gln
 65                  70                  75                  80

Glu Asp Phe Ala Thr Tyr Phe Cys Gln Gln Gly Asn Thr Leu Pro Trp
                 85                  90                  95

Thr Phe Gly Gly Gly Thr Lys Leu Glu Ile Lys
            100                 105
```

```
<210> SEQ ID NO 3
<211> LENGTH: 369
<212> TYPE: DNA
<213> ORGANISM: Mus sp.
<220> FEATURE:
<223> OTHER INFORMATION: RFB4 mouse IgG1 anti-human CD22 monoclonal
      antibody heavy chain variable region (VH)
<220> FEATURE:
<221> NAME/KEY: CDS
<222> LOCATION: (1)..(369)
<223> OTHER INFORMATION: RFB4 mouse IgG1 anti-human CD22 monoclonal
      antibody heavy chain variable region (VH)

<400> SEQUENCE: 3

gaa gtg cag ctg gtg gag tct ggg gga ggc tta gtg aag cct gga ggg       48
Glu Val Gln Leu Val Glu Ser Gly Gly Gly Leu Val Lys Pro Gly Gly
  1               5                  10                  15

tcc ctg aaa ctc tcc tgt gca gcc tct gga ttc gct ttc agt atc tat       96
Ser Leu Lys Leu Ser Cys Ala Ala Ser Gly Phe Ala Phe Ser Ile Tyr
             20                  25                  30

gac atg tct tgg gtt cgc cag act ccg gag aag agg ctg gag tgg gtc      144
Asp Met Ser Trp Val Arg Gln Thr Pro Glu Lys Arg Leu Glu Trp Val
         35                  40                  45

gca tac att agt agt ggt ggt ggt acc acc tac tat cca gac act gtg      192
Ala Tyr Ile Ser Ser Gly Gly Gly Thr Thr Tyr Tyr Pro Asp Thr Val
     50                  55                  60

aag ggc cga ttc acc atc tcc aga gac aat gcc aag aac acc ctg tac      240
Lys Gly Arg Phe Thr Ile Ser Arg Asp Asn Ala Lys Asn Thr Leu Tyr
 65                  70                  75                  80

ctg caa atg agc agt ctg aag tct gag gac aca gcc atg tat tac tgt      288
Leu Gln Met Ser Ser Leu Lys Ser Glu Asp Thr Ala Met Tyr Tyr Cys
                 85                  90                  95

gca aga cat agt ggc tac ggt agt agc tac ggg gtt ttg ttt gct tac      336
Ala Arg His Ser Gly Tyr Gly Ser Ser Tyr Gly Val Leu Phe Ala Tyr
            100                 105                 110

tgg ggc caa ggg act ctg gtc act gtc tct gca                          369
Trp Gly Gln Gly Thr Leu Val Thr Val Ser Ala
        115                 120


<210> SEQ ID NO 4
<211> LENGTH: 123
<212> TYPE: PRT
<213> ORGANISM: Mus sp.
<220> FEATURE:
<223> OTHER INFORMATION: RFB4 mouse IgG1 anti-human CD22 monoclonal
      antibody heavy chain variable region (VH)

<400> SEQUENCE: 4

Glu Val Gln Leu Val Glu Ser Gly Gly Gly Leu Val Lys Pro Gly Gly
  1               5                  10                  15

Ser Leu Lys Leu Ser Cys Ala Ala Ser Gly Phe Ala Phe Ser Ile Tyr
             20                  25                  30

Asp Met Ser Trp Val Arg Gln Thr Pro Glu Lys Arg Leu Glu Trp Val
         35                  40                  45

Ala Tyr Ile Ser Ser Gly Gly Gly Thr Thr Tyr Tyr Pro Asp Thr Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Ser Gly Tyr Gly Ser Ser Tyr Gly Val Leu Phe Ala Tyr
            100                 105                 110
```

```
Trp Gly Gln Gly Thr Leu Val Thr Val Ser Ala
        115                 120


<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:carboxyl
      terminal fragment binding KDEL recycling receptor
      for transport of construct into cytosol from
      endoplasmic reticulum

<400> SEQUENCE: 5

Lys Asp Glu Leu
  1


<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:carboxyl
      terminal fragment binding KDEL recycling receptor
      for transport of construct into cytosol from
      endoplasmic reticulum

<400> SEQUENCE: 6

Arg Glu Asp Leu
  1


<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:RFB4
      variable light chain (VL) complementarity determining
      region 1 (CDR1)

<400> SEQUENCE: 7

Gln Asp Ile His Gly Tyr
  1               5


<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:RFB4
      variable light chain (VL) complementarity determining
      region 1 (CDR1)

<400> SEQUENCE: 8

Gln Asp Ile Gly Arg Tyr
  1               5


<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:RFB4
      variable light chain (VL) complementarity determining
      region 1 (CDR1)

<400> SEQUENCE: 9

Gln Asp Ile Arg Gly Tyr
  1               5
```

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:RFB4 variable light chain (VL) complementarity determining region 1 (CDR1)

<400> SEQUENCE: 10

Gln Asp Ile Ala Arg Tyr
1 5

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:RFB4 variable light chain (VL) complementarity determining region 2 (CDR2)

<400> SEQUENCE: 11

Tyr Thr Ser
1

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:RFB4 variable light chain (VL) complementarity determining region 3 (CDR3)

<400> SEQUENCE: 12

Gln Gln Gly Asn Thr Leu Pro Trp Thr
1 5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence:RFB4 variable heavy chain (VH) complementarity determining region 1 (CDR1)

<400> SEQUENCE: 13

Gly Phe Ala Phe Ser Ile Tyr Asp
1 5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:RFB4 variable heavy chain (VH) complementarity determining region 2 (CDR2)

<400> SEQUENCE: 14

Ile Ser Ser Gly Gly Gly Thr Thr
1 5

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence:RFB4
variable heavy chain (VH) complementarity determining
region 3 (CDR3)

<400> SEQUENCE: 15

```
Ala Arg His Ser Gly Tyr Gly Ser Ser Tyr Gly Val Leu Phe Ala Tyr
  1               5                  10                  15
```

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence:RFB4
variable heavy chain (VH) complementarity determining
region 3 (CDR3)

<400> SEQUENCE: 16

```
Ala Arg His Ser Gly Tyr Gly Thr His Trp Gly Val Leu Phe Ala Tyr
  1               5                  10                  15
```

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence:RFB4
variable heavy chain (VH) complementarity determining
region 3 (CDR3)

<400> SEQUENCE: 17

```
Ala Arg His Ser Gly Tyr Gly Tyr Asn Trp Gly Val Leu Phe Ala Tyr
  1               5                  10                  15
```

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence:RFB4
variable heavy chain (VH) complementarity determining
region 3 (CDR3)

<400> SEQUENCE: 18

```
Ala Arg His Ser Gly Tyr Gly Thr Thr Trp Gly Val Leu Phe Ala Tyr
  1               5                  10                  15
```

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence:RFB4
variable heavy chain (VH) complementarity determining
region 3 (CDR3)

<400> SEQUENCE: 19

```
Ala Arg His Ser Gly Tyr Gly Ser Thr Tyr Gly Val Leu Phe Ala Tyr
  1               5                  10                  15
```

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence:mutated RFB4
VL chain

<400> SEQUENCE: 20

```
Asp Ile Gln Met Thr Gln Thr Thr Ser Ser Leu Ser Ala Ser Leu Gly
  1               5                  10                  15

Asp Arg Val Thr Ile Ser Cys Arg Ala Ser Gln Asp Ile His Gly Tyr
             20                  25                  30

Leu Asn Trp Tyr Gln Gln Lys Pro Asp Gly Thr Val Lys Leu Leu Ile
         35                  40                  45

Tyr Tyr Thr Ser Ile Leu His Ser Gly Val Pro Ser Arg Phe Ser Gly
     50                  55                  60

Ser Gly Ser Gly Thr Asp Tyr Ser Leu Thr Ile Ser Asn Leu Glu Gln
 65                  70                  75                  80

Glu Asp Phe Ala Thr Tyr Phe Cys Gln Gln Gly Asn Thr Leu Pro Trp
                 85                  90                  95

Thr Phe Gly Gly Gly Thr Lys Leu Glu Ile Lys
            100                 105


<210> SEQ ID NO 21
<211> LENGTH: 123
<212> TYPE: PRT
<213> ORGANISM: Artificial Sequence
<220> FEATURE:
<223> OTHER INFORMATION: Description of Artificial Sequence:mutated RFB4
      VH chain

<400> SEQUENCE: 21

Glu Val Gln Leu Val Glu Ser Gly Gly Gly Leu Val Lys Pro Gly Gly
  1               5                  10                  15

Ser Leu Lys Leu Ser Cys Ala Ala Ser Gly Phe Ala Phe Ser Ile Tyr
             20                  25                  30

Asp Met Ser Trp Val Arg Gln Thr Pro Glu Lys Arg Leu Glu Trp Val
         35                  40                  45

Ala Tyr Ile Ser Ser Gly Gly Gly Thr Thr Tyr Tyr Pro Asp Thr Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Ser Gly Tyr Gly Thr His Trp Gly Val Leu Phe Ala Tyr
            100                 105                 110

Trp Gly Gln Gly Thr Leu Val Thr Val Ser Ala
        115                 120


<210> SEQ ID NO 22
<211> LENGTH: 345
<212> TYPE: PRT
<213> ORGANISM: Artificial Sequence
<220> FEATURE:
<223> OTHER INFORMATION: Description of Artificial Sequence:Pseudomonas
      exotoxin A cytotoxic fragment PE38 translocating
      and ADP ribosylating domains

<400> SEQUENCE: 22

Gly Gly Ser Leu Ala Ala Leu Thr Ala His Gln Ala Cys His Leu Pro
  1               5                  10                  15

Leu Glu Thr Phe Thr Arg His Arg Gln Pro Arg Gly Trp Glu Gln Leu
             20                  25                  30

Glu Gln Cys Gly Tyr Pro Val Gln Arg Leu Val Ala Leu Tyr Leu Ala
         35                  40                  45

Ala Arg Leu Ser Trp Asn Gln Val Asp Gln Val Ile Arg Asn Ala Leu
     50                  55                  60
```

```
Ala Ser Pro Gly Ser Gly Gly Asp Leu Gly Glu Ala Ile Arg Glu Gln
 65                  70                  75                  80

Pro Glu Gln Ala Arg Leu Ala Leu Thr Leu Ala Ala Ala Glu Ser Glu
                85                  90                  95

Arg Phe Val Arg Gln Gly Thr Gly Asn Asp Glu Ala Gly Ala Ala Asn
            100                 105                 110

Gly Pro Ala Asp Ser Gly Asp Ala Leu Leu Glu Arg Asn Tyr Pro Thr
        115                 120                 125

Gly Ala Glu Phe Leu Gly Asp Gly Gly Asp Val Ser Phe Ser Thr Arg
    130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
            180                 185                 190

Asp Leu Asp Ala Ile Trp Arg Gly Phe Tyr Ile Ala Gly Asp Pro Ala
        195                 200                 205

Leu Ala Tyr Gly Tyr Ala Gln Asp Gln Glu Pro Asp Ala Arg Gly Arg
    210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Glu Gly Gly Arg Leu Glu Thr Ile Leu
        275                 280                 285

Gly Trp Pro Leu Ala Glu Arg Thr Val Val Ile Pro Ser Ala Ile Pro
    290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Glu Asp Leu Lys
            340                 345
```

<210> SEQ ID NO 23
<211> LENGTH: 345
<212> TYPE: PRT
<213> ORGANISM: Artificial Sequence
<220> FEATURE:
<223> OTHER INFORMATION: Description of Artificial Sequence:Pseudomonas exotoxin A cytotoxic fragment PE38 translocating and ADP ribosylating domains with Arg at position 222 of PE38 (position 490 of Pseudomonas exotoxin A) mutated to Ala

<400> SEQUENCE: 23

```
Gly Gly Ser Leu Ala Ala Leu Thr Ala His Gln Ala Cys His Leu Pro
  1               5                  10                  15

Leu Glu Thr Phe Thr Arg His Arg Gln Pro Arg Gly Trp Glu Gln Leu
             20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
     50                  55                  60
```

```
Ala Ser Pro Gly Ser Gly Gly Asp Leu Gly Glu Ala Ile Arg Glu Gln
 65                 70                  75                  80

Pro Glu Gln Ala Arg Leu Ala Leu Thr Leu Ala Ala Ala Glu Ser Glu
                85                  90                  95

Arg Phe Val Arg Gln Gly Thr Gly Asn Asp Glu Ala Gly Ala Ala Asn
            100                 105                 110

Gly Pro Ala Asp Ser Gly Asp Ala Leu Leu Glu Arg Asn Tyr Pro Thr
        115                 120                 125

Gly Ala Glu Phe Leu Gly Asp Gly Gly Asp Val Ser Phe Ser Thr Arg
    130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
            180                 185                 190

Asp Leu Asp Ala Ile Trp Arg Gly Phe Tyr Ile Ala Gly Asp Pro Ala
        195                 200                 205

Leu Ala Tyr Gly Tyr Ala Gln Asp Gln Glu Pro Asp Ala Ala Gly Arg
    210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Glu Gly Gly Arg Leu Glu Thr Ile Leu
        275                 280                 285

Gly Trp Pro Leu Ala Glu Arg Thr Val Val Ile Pro Ser Ala Ile Pro
    290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Glu Asp Leu Lys
            340                 345


<210> SEQ ID NO 24
<211> LENGTH: 613
<212> TYPE: PRT
<213> ORGANISM: Pseudomonas sp.
<220> FEATURE:
<223> OTHER INFORMATION: Pseudomonas exotoxin A

<400> SEQUENCE: 24

Ala Glu Glu Ala Phe Asp Leu Trp Asn Glu Cys Ala Lys Ala Cys Val
  1               5                  10                  15

Leu Asp Leu Lys Asp Gly Val Arg Ser Ser Arg Met Ser Val Asp Pro
             20                  25                  30

Ala Ile Ala Asp Thr Asn Gly Gln Gly Val Leu His Tyr Ser Met Val
         35                  40                  45

Leu Glu Gly Gly Asn Asp Ala Leu Lys Leu Ala Ile Asp Asn Ala Leu
     50                  55                  60

Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
```

-continued

```
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510
```

-continued

```
Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610


<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:two-step
      overlap PCR upstream mutagenic primer A

<400> SEQUENCE: 25

gaacccgacg cagccggccg tatccgcaac                                       30


<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:two-step
      overlap PCR downstream mutagenic primer B

<400> SEQUENCE: 26

gttgcggata cggccggctg cgtcgggttc                                       30


<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence:two-step
      overlap PCR mutagenic primer C

<400> SEQUENCE: 27

gctgtcgtgg aaccaggtcg accagg                                           26


<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence:two-step
      overlap PCR mutagenic primer D

<400> SEQUENCE: 28

ctttgttagc agccgaattc atattcgat                                        29


<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence:RFB4 VH
```

-continued

```
      chain CDR3 in which "SSY" mutated to "THW"

<400> SEQUENCE: 29

Gly Thr His Trp
  1


<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence:carboxyl
      terminal native sequence binding KDEL recycling
      receptor for transport of construct into cytosol
      from endoplasmic reticulum

<400> SEQUENCE: 30

Arg Glu Asp Leu Lys
  1             5
```

MUTATED ANTI-CD22 ANTIBODIES AND IMMUNOCONJUGATES

CROSS-REFERENCES TO RELATED APPLICATIONS

This application claims the benefit of and priority from U.S. Provisional Application No. 60/525,371, filed Nov. 25, 2003, the contents of which are incorporated by reference.

STATEMENT AS TO RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

Hematological malignancies are a major public health problem. It has been estimated that in the year 2000, more than 50,000 new cases of non-Hodgkin's lymphoma and more than 30,000 new cases of leukemia occurred in the United States (Greenlee, R. T. et al., *CA Cancer J. Clin.,* 50:7-33 (2000)) and more than 45,000 deaths were expected from these diseases. Many more patients live with chronic disease-related morbidity. Unfortunately, in a high percentage of patients, conventional therapies are not able to induce long term complete remissions.

In the past several years immunotoxins have been developed as an alternative therapeutic approach to treat these malignancies. Immunotoxins were originally composed of an antibody chemically conjugated to a plant or a bacterial toxin. The antibody binds to the antigen expressed on the target cell and the toxin is internalized causing cell death by arresting protein synthesis and inducing apoptosis (Brinkmann, U., *Mol. Med. Today,* 2:439-446 (1996)).

Hematological malignancies are an attractive target for immunotoxin therapies because tumor cells are easily accessible and the target antigens are highly expressed (Kreitman, R. J. and Pastan, I., *Semin. Cancer Biol.,* 6:297-306 (1995)). One of these antigens is CD25. A clinical trial with immunotoxin LMB-2 (anti-Tac(Fv)-PE38) that targets CD25 showed that the agent was well tolerated and that it had substantial anti-tumor activity (Kreitman, R. J. et al., *Blood,* 94:3340-3348 (1999); Kreitman, R. J. et al., *J. Clin. Oncol.,* 18:16222-1636 (2000)). A complete response was observed in one patient with Hairy Cell Leukemia and partial responses were observed in patients with Hairy Cell Leukemia, chronic lymphocytic leukemia, cutaneous T cell lymphoma, Hodgkins disease and adult T cell leukemia.

Another antigen that has been used as an immunotoxin target is CD22, a lineage-restricted B cell antigen expressed in 60-70% of B cell lymphomas and leukemias. CD22 is not present on the cell surface in the early stages of B cell development and is not expressed on stem cells (Tedder, T. F. et al., *Annu. Rev. Immunol.,* 5:481-504 (1997)). Clinical trials have been conducted with an immunotoxin containing an anti-CD22 antibody, RFB4, or its Fab fragment, coupled to deglycosylated ricin A. In these trials, substantial clinical responses have been observed; however, severe and in certain cases fatal, vascular leak syndrome was dose limiting (Sausville, E. A. et al., *Blood,* 85:3457-3465 (1995); Amlot, P. L. et al., *Blood,* 82:2624-2633 (1993); Vitetta, E. S. et al., *Cancer Res.,* 51:4052-4058 (1991)).

As an alternative approach, the RFB4 antibody was used to make a recombinant immunotoxin in which the Fv fragment in a single chain form is fused to a 38 kDa truncated form of *Pseudomonas* exotoxin A (PE38, SEQ ID NO:22). PE38 contains the translocating and ADP ribosylating domains of PE but not the cell-binding portion (Hwang, J. et al., *Cell,* 48:129-136 (1987)). RFB4 (Fv)-PE38 is cytotoxic towards CD22-positive cells (Mansfield, E. et al., *Biochem. Soc. Trans.,* 25:709-714 (1997)). To stabilize the single chain Fv immunotoxin and to make it more suitable for clinical development, cysteine residues were engineered into framework regions of the $V_H$ and $V_L$ (Mansfield, E. et al., *Blood,* 90:2020-2026 (1997)) generating the molecule RFB4 (dsFv)-PE38.

RFB4 (dsFv)-PE38 is able to kill leukemic cells from patients and induced complete remissions in mice bearing lymphoma xenografts (Kreitman, R. J. et al., *Clin. Cancer Res.,* 6:1476-1487 (2000); Kreitman, R. J. et al., *Int. J. Cancer,* 81:148-155 (1999)). RFB4 (dsFv)-PE38 (BL22) was evaluated in a phase I clinical trial at the National Cancer Institute in patients with hematological malignancies. Sixteen patients with purine analogue resistant hairy cell leukemia were treated with BL22 and eleven (86%) achieved complete remissions.

These results show that BL22 is the first agent that is able to induce high complete remission rate in patients with purine analogue-resistant HCL and establish the concept that immunotoxins can produce clinical benefit to patients with advanced malignancies (Kreitman, R. J., et al., *N Engl J Med,* 345(4):241-7 (2001)).

HA22 is a recently developed, improved form of BL22. To produce this immunotoxin, the binding region of antibody RFB4 was mutated and antibody phage display was used to isolate mutant phage that bound better to CD22 because of mutations in CDR3 of the heavy chain. In HA22, residues SSY in the CDR3 of the antibody variable region heavy chain ("$V_H$") were mutated to THW. Compared to its parental antibody, RFB4, HA22 has a 5-10-fold increase in cytotoxic activity on various CD22-positive cell lines and is up to 50 times more cytotoxic to cells from patients with CLL and HCL (Salvatore, G., et al., *Clin Cancer Res,* 8(4):995-1002 (2002); see also, co-owned application PCT/US02/30316, International Publication WO 03/027135).

BL22 appears to work well on malignancies, such as HCL, which express significant amounts of CD22. It showed much less activity, however, in chronic lymphocytic leukemia (CLL), in which the cells express only small amounts of CD22. As noted above, HA22-based immunotoxin is much more cytotoxic to cells from persons with CLL than is BL22. Given the low density of CD22 on CLL cells, however, it would be desirable to improve targeting to CLL cells further by developing antibodies with even greater affinity to CD22 than that of HA22.

Unfortunately, the factors that influence binding affinity are multifaceted and obtaining mutant scFvs with improved affinity is not trivial. Although antibody-antigen crystal structure can suggest which residues are involved in binding, atomic resolution structural data are not available for most antibodies. Moreover, even when such data is available it cannot generally be predicted which residues and which mutations will result in an antibody with increased antigen binding activity.

Even if immunotoxins bind tightly to the surface of targeted cells, however, death of the targeted cell is not assured. Commonly used toxins (e.g., diphtheria toxin, gelonin, ricin, and PE) act at the ribosomal level to inactivate protein synthesis. Thus, the toxin must be correctly routed to the ribosome for cell death to occur. For immunotoxins targeted to specific cell-surface receptors, this involves receptor-mediated endocytosis into an appropriate intracellular vesicle, followed by translocation of the toxin across the vesicular membrane to the cytosol. Inefficient intracellular trafficking, e.g, immunotoxins traveling to lysosomes, results in a large reduction in utilization of the targeted toxin (Thrush, G. R., et al., *Annu Rev Immunol,* 14:49-71 (1996)).

Thus, in addition to increasing the affinity of antibodies such as BL22 or HA22 to CD22, another way to increase the cytotoxicity of immunotoxins to CLL cells would be to increase the cytotoxicity of the toxin moiety. As noted above, a clinical trial of BL22 used as the toxic moiety a form of *Pseudomonas* exotoxin A ("PE") truncated to reduce non-specific toxicity, and PE has been used in clinical trials with other targeting agents. Given PE's utility in therapeutic agents, it would be useful to further improve PE's toxicity. But the complicated manner in which PE exerts its toxicity renders improving that toxicity problematic.

Based on the crystallographic structure of PE (Allured, V. S., et al., *Proc Natl Acad Sci USA,* 83(5):1320-4 (1986)) and many functional studies, BL22 is thought to kill target cells in the circulation by the following steps. First, in the circulation, the carboxy terminal lysine residue is removed (Hessler, J. L., et al., *Biochemistry,* 36(47):14577-82 (1997)). Next, the Fv portion of the immunotoxin binds to CD22 on the surface of the target cell, and the molecule is internalized into the endocytic compartment, where the protease furin cleaves the toxin between amino acids 279 and 280 of PE (Chiron, M. F., et al., *J Biol Chem,* 269(27):18167-76 (1994); Ogata, M., et al., *J Biol Chem,* 265(33):20678-85 (1990)). Subsequently, the disulfide bond linking cysteines at positions 265 and 287 is reduced producing two fragments. Then the REDL (SEQ ID NO:6) sequence on the carboxyl terminal fragment binds to the KDEL (SEQ ID NO:5) recycling receptor and the fragment containing part of domain 2 and all of domain 3 is transported from the trans-reticular Golgi to the endoplasmic reticulum (ER) (Kreitman, R. J., et al., *Semin Cancer Biol,* 6(5):297-306 (1995)). Once there, amino acids 280-313 somehow facilitate translocation of the toxin into the cytosol, probably taking advantage of preexisting pores in the ER (Theuer, C. P., et al., *Proc Natl Acad Sci USA,* 90(16):7774-8 (1993); Theuer, C., et al., *Biochemistry,* 33(19):5894-900 (1994)). In the cytosol, the ADP ribosylation activity located within domain III of PE catalytically inactivates elongation factor 2, inhibiting protein synthesis and leading to cell death.

The present invention provides solutions to some of these difficult problems.

BRIEF SUMMARY OF THE INVENTION

In a first group of embodiments, the present invention provides improved antibodies that specifically bind CD22. The antibodies have a variable light (VL) chain comprising three complementarity determining regions (CDRs) designated in order from the CDR closest to the amino terminus to the CDR closest to the carboxyl terminus CDRs 1, 2, and 3, wherein the said CDR1 has a sequence selected from the group consisting of SEQ ID NOs:7, 8, 9, and 10. In some embodiments, the CDR1 of the antibody VL has the sequence of SEQ ID NO:7. Further, in some embodiments, the CDR 2 of the antibody VL has the sequence of SEQ ID NO:11, and CDR3 has the sequence of SEQ ID NO:12. In some embodiments, the VL chain has the sequence of SEQ ID NO:20.

The antibody can further compre a variable heavy (VH) chain comprising three complementarity determining regions (CDRs) designated in order from the CDR closest to the amino terminus to the CDR closest to the carboxyl terminus CDRs 1, 2, and 3, wherein the CDR1 has the sequence of SEQ ID NO:13, the CDR2 has the sequence of SEQ ID NO:15 SEQ ID NO:14, and the CDR3 has a sequence selected from the group consisting of SEQ ID NOs:15, 16, 17, 18, and 19. In some embodiments, the CDR3 has the sequence of SEQ ID NO:16. In some embodiments, the VH chain has the sequence of SEQ ID NO:21. The antibody can be, for example, an scFv, a dsFv, a Fab, or a F(ab')2.

In another group of embodiments, the invention provides chimeric molecules comprising (a) an antibody that specifically binds CD22, which antibody has a variable light (VL) chain comprising three complementarity determining regions (CDRs) designated in order from the CDR closest to the amino terminus to the CDR closest to the carboxyl terminus CDRs 1, 2, and 3, wherein the CDR1 has a sequence selected from the group consisting of SEQ ID NOs:7, 8, 9, and 10; and (b) a therapeutic moiety or a detectable label. The therapeutic moiety or a detectable label can be conjugated or fused to the antibody. In some embodiments, the CDR2 of the chimeric molecule has the sequence of SEQ ID NO:11, and the CDR3 has the sequence of SEQ ID NO:12. The antibody portion of the chimeric molecule can further comprise a variable heavy (VH) chain comprising three complementarity determining regions (CDRs) designated in order from the CDR closest to the amino terminus to the CDR closest to the carboxyl terminus CDRs 1, 2, and 3, wherein the CDR1 has the sequence of SEQ ID NO:13, the CDR 2 has the sequence of SEQ ID NO:14, and the CDR3 has a sequence selected from the group consisting of SEQ ID NOs:15, 16, 17, 18, and 19. In some embodiments, the VL chain has the sequence of SEQ ID NO:20 and the VH chain has the sequence of SEQ ID NO:21. The therapeutic moiety can be, for example, a cytotoxin, a drug, a radioisotope, or a liposome loaded with a drug or a cytotoxin. In some embodiments, the therapeutic moiety is a cytotoxin is selected from the group consisting of ricin A, abrin, ribotoxin, ribonuclease, saporin, calicheamycin, diphtheria toxin, or a cytotoxic fragment or mutant thereof, Pseudomonas exotoxin A or a cytotoxic fragment or mutant thereof ("PE"), or botulinum toxin A through F. In some embodiments, the PE is selected from the group consisting of PE35, PE38, PE38 KDEL, PE40, PE4E, and PE38QQR. In some embodiments, the PE has a substituent of glycine, alanine, valine, leucine, or isoleucine in place of arginine at the position corresponding to position 490 of SEQ ID NO:24. In a preferred embodiment, the substituent at position 490 is alanine.

In yet another group of embodiments, the invention provides compositions comprising any of the chimeric molecules described in the preceding paragraph, and a pharmaceutically acceptable carrier.

In yet another group of embodiments, the invention provides for the use of an antibody that specifically binds CD22, the anti-CD22 antibody having a variable light (VL) chain comprising three complementarity determining regions (CDRs), the CDRs designated in order from the CDR closest to the amino terminus to the CDR closest to the carboxyl terminus as CDRs 1, 2, and 3, respectively, wherein CDR1 has a sequence selected from the group consisting of SEQ ID NOs:7, 8, 9, and 10, for the manufacture of a medicament to inhibit the growth of a CD22+ cancer cell. In some embodiments, the CDR 2 has the sequence of SEQ ID NO:11, and the CDR3 has the sequence of SEQ ID NO:12. The antibody can further comprise a variable heavy (VH) chain comprising three complementarity determining regions (CDRs), the CDRs being designated in order from the CDR closest to the amino terminus to the CDR closest to the carboxyl terminus as CDRs 1, 2, and 3, respectively, wherein the CDR1 has the sequence of SEQ ID NO:13, the CDR 2 has the sequence of SEQ ID NO:14, and the CDR3 has a sequence selected from the group consisting of SEQ ID NOs:15, 16, 17, 18, and 19. In some embodiments, the VL chain has the sequence of SEQ ID NO:20 and said VH chain has the sequence of SEQ ID NO:21. The antibody can be, for example, an scFv, dsFv, a Fab, or a F(ab')2. The antibody can be attached to a therapeutic moiety or a detectable label. Where the antibody is attached to a therapeutic moiety, the therapeutic moiety can be, for example, a cytotoxin, a drug, a radioisotope, or a liposome loaded with a drug or a cytotoxin. In some preferred embodiments, the therapeutic moiety is a cytotoxin. In some embodiments, the cytotoxin is selected from the group consisting of ricin A, abrin, ribotoxin, ribonuclease, saporin, calicheamycin, diphtheria toxin or a cytotoxic fragment or mutant thereof, a Pseudomonas exotoxin A or a cytotoxic fragment or mutant thereof ("PE"), and botulinum toxins A through F. Where the cytotoxin is PE, the PE can be, for example, PE35, PE38, PE38 KDEL, PE40, PE4E, or PE38QQR. In some preferred embodiments, the PE has a glycine, alanine, valine, leucine, or isoleucine in place of arginine at the position corresponding to position 490 of SEQ ID NO:24. In a preferred embodiment, alanine is substituted for arginine at position 490.

In still another group of embodiments, the invention provides isolated nucleic acids encoding a variable light (VL) chain comprising three complementarity determining regions (CDRs), the CDRs being designated in order from the CDR closest to the amino terminus to the CDR closest to the carboxyl terminus as CDRs 1, 2, and 3, respectively, wherein the CDR1 has a sequence selected from the group consisting of SEQ ID NOs:7, 8, 9, and 10. In some embodiments, the CDR 2 has the sequence of SEQ ID NO:11, and the CDR3 has the sequence of SEQ ID NO:12. The nucleic acids can further encode a variable heavy (VH) chain comprising three complementarity determining regions (CDRs), the CDRs designated in order from the CDR closest to the amino terminus to the CDR closest to the carboxyl terminus CDRs 1, 2, and 3, respectively, wherein the CDR1 has the sequence of SEQ ID NO:13, the CDR 2 has the sequence of SEQ ID NO:14, and the CDR3 has a sequence selected from the group consisting of SEQ ID NOs:15, 16, 17, 18, and 19. In some embodiments the VL chain has the sequence of SEQ ID NO:20 and the VH chain of said encoded antibody has the sequence of SEQ ID NO:21. In some embodiments, the nucleic acid encodes an antibody selected from the group consisting of an scFv, a dsFv, a Fab, or a F(ab')2. In some embodiments, the nucleic acid further encodes a polypeptide which is a therapeutic moiety or a detectable label. Where the nucleic acid encodes a therapeutic moiety, the moiety can be, for example, a drug or a cytotoxin. Where it is a cytotoxin, it can be, for example, *Pseudomonas* exotoxin A or a cytotoxic fragment or mutant thereof ("PE"). The PE can be, for example, PE35, PE38, PE38 KDEL, PE40, PE4E, or PE38QQR. In some embodiments, the PE has a glycine, alanine, valine, leucine, or isoleucine in place of arginine at the position corresponding to position 490 of SEQ ID NO:24. In preferred embodiments, alanine is substituted for arginine at position 490.

In still further embodiments, the invention provides expression vectors comprising one of the isolated nucleic acids described in the preceding paragraph, operably linked to a promoter.

In another group of embodiments, the invention provides methods of inhibiting growth of a CD22+ cancer cell by contacting said cell with a chimeric molecule comprising (a) an antibody that binds to CD22, the antibody having a variable light (VL) chain comprising three complementarity determining regions (CDRs), the CDRs designated in order from the CDR closest to the amino terminus to the CDR closest to the carboxyl terminus CDRs 1, 2, and 3, respectively, wherein the CDR1 has a sequence selected from the group consisting of SEQ ID NOs:7, 8, 9, and 10, and (b) a therapeutic moiety, wherein the therapeutic moiety inhibits the growth of said cell. In some embodiments, the CDR 2 of said VL has the sequence of SEQ ID NO:11, and the CDR3 of said VL has the sequence of SEQ ID NO:12. In some embodiments, the antibody comprises a VH chain comprising three complementarity determining regions (CDRs), the CDRs designated in order from the CDR closest to the amino terminus to the CDR closest to the carboxyl terminus CDRs 1, 2, and 3, respectively, wherein the CDR1 has the sequence of SEQ ID NO:13, the CDR 2 has the sequence of SEQ ID NO:14, and the CDR3 has a sequence selected from the group consisting of SEQ ID NOs:15, 16, 17, 18, and 19. In some of the methods, the VL chain has the sequence of SEQ ID NO:20 and said VH chain has the sequence of SEQ ID NO:21. The antibody can be, for example, an scFv, a dsFv, a Fab, or a F(ab')2. The therapeutic moiety can be, for example, a cytotoxin, a drug, a radioisotope, or a liposome loaded with a drug or a cytotoxin. Where the therapeutic moiety is a cytotoxin, the cytotoxin can be, for example, ricin A, abrin, ribotoxin, ribonuclease, saporin, calicheamycin, diphtheria toxin or a cytotoxic fragment or mutant thereof, *Pseudomonas* exotoxin A or a cytotoxic fragment or mutant thereof ("PE"), or botulinum toxin A through F. The PE can be, for example, consisting of PE35, PE38, PE38 KDEL, PE40, PE4E, and PE38QQR. Where the cytotoxin is PE, the PE can have a glycine, alanine, valine, leucine, or isoleucine in place of arginine at the position corresponding to position 490 of SEQ ID NO:24. In a preferred embodiment, alanine is substituted for arginine at a position corresponding to position 490 of SEQ ID NO:24.

In yet another group of embodiments, the invention provides methods for detecting the presence of a CD22+ cancer cell in a biological sample. The methods comprise (a) contacting cells of the biological sample with a chimeric molecule comprising (i) an antibody that specifically binds to CD22, the antibody having a variable light (VL) chain comprising three complementarity determining regions (CDRs), the CDRs designated in order from the CDR closest to the amino terminus to the CDR closest to the carboxyl terminus CDRs 1, 2, and 3, respectively, wherein the CDR1 has a sequence selected from the group consisting of SEQ ID NOs: 7, 8, 9, and 10, conjugated or fused to (ii) a detectable label; and, (b) detecting the presence or absence of said label, wherein detecting the presence of said label indicates the presence of a CD22+ cancer cell in said sample. In some embodiments, the CDR 2 of said VL of said antibody has the sequence of SEQ ID NO:11, and the CDR3 of the VL of said antibody has the sequence of SEQ ID NO:12. In some embodiments, the antibody further comprises a variable heavy (VII) chain comprising three complementarity determining regions (CDRs), the CDRs designated in order from the CDR closest to the amino terminus to the CDR closest to the carboxyl terminus CDRs 1, 2, and 3, respectively, wherein the CDR1 has the sequence of SEQ ID NO:13, the CDR 2 has the sequence of SEQ ID NO:14, and the CDR3 has a sequence selected from the group consisting of SEQ ID NOs:15, 16, 17, 18, and 19. In some embodiments, the VL chain has the sequence of SEQ ID NO:20 and the V11 chain has the sequence of SEQ ID NO:21. The antibody can be, for example, an scFv, a dsFv, a Fab, or a F(ab')2.

In yet another group of embodiments, the invention provides kits. The kits comprise (a) a container, and (b) a chimeric molecule comprising (i) an anti-CD22 antibody having a variable light (VL) chain comprising three complementarity determining regions (CDRs), the CDRs designated in order from the CDR closest to the amino terminus to the CDR closest to the carboxyl terminus CDRs 1, 2, and 3, respectively, wherein the CDR1 has a sequence selected from the group consisting of SEQ ID NOs:7, 8, 9, and 10, conjugated or fused to (ii) a detectable label or a therapeutic moiety. In some embodiments, the CDR 2 of the VL of the antibody has the sequence of SEQ ID NO:11, and the CDR3 of the VL of the antibody has the sequence of SEQ ID NO:12. In some embodiments, the antibody further comprises a variable heavy (VH) chain comprising three complementarity determining regions (CDRs) designated in order from the CDR closest to the amino terminus to the CDR closest to the carboxyl terminus CDRs 1, 2, and 3, wherein the CDR1 has the sequence of SEQ ID NO:13, the CDR 2 has the sequence of SEQ ID NO:14, and the CDR3 has a sequence selected from the group consisting of SEQ ID NOs:15, 16, 17, 18, and 19. In some embodiments, the VL chain has the sequence of SEQ ID NO:20 and the VH chain has the sequence of SEQ ID NO:21. The antibody can be, for example, an scFv, a dsFv, a Fab, or a F(ab')2. The therapeutic moiety can be, for example, a cytotoxin, a drug, a radioisotope, or a liposome loaded with a drug or a cytotoxin.

In still another group of embodiments, the invention provides *Pseudomonas* exotoxin A or cytotoxic fragments or mutants thereof, wherein the PE has a glycine, alanine, valine, leucine, or isoleucine in place of arginine at the position corresponding to position 490 of SEQ ID NO:24. The PE can be, for example, PE35, PE38, PE38KDEL, PE40, PE4E, or PE38QQR. In some preferred embodiments, the PE has an alanine at the position corresponding to position 490 of SEQ ID NO:24.

The invention further provides chimeric molecules comprising a targeting moiety conjugated or fused to a *Pseudomonas* exotoxin A or cytotoxic fragments or mutants thereof ("PE"), wherein the PE has a glycine, alanine, valine, leucine, or isoleucine in place of arginine at the position corresponding to position 490 of SEQ ID NO:24. The PE can be, for example, PE35, PE38, PE38KDEL, PE40, PE4E, or PE38QQR In some preferred embodiments, the PE has an alanine at a position corresponding to position 490 of SEQ ID NO:24. In some embodiments, the targeting moiety is an antibody. The antibody can be, for example, an scFv, a dsFv, a Fab, or a F(ab')2.

The invention further provides compositions comprising any of the chimeric molecules described in the preceding paragraph and a pharmaceutically acceptable carrier.

In yet another group of embodiments, the invention provides isolated nucleic acids encoding *Pseudomonas* exotoxin A or a cytotoxic fragment or a mutant thereof ("PE"), wherein the PE has a glycine, alanine, valine, leucine, or isoleucine in place of arginine at a position corresponding to position 490 of SEQ ID NO:24. The PE can be, for example, PE35, PE38, PE38KDEL, PE40, PE4E, or PE38QQR. In a preferred embodiment, the PE has an alanine at the position corresponding to position 490 of SEQ ID NO:24. The nucleic acid can further encode a targeting moiety. The targeting moiety can be an antibody. The antibody can be, for example, an scFv, a dsFv, a Fab, or a F(ab')2.

The invention further provides expression vectors comprising any of the nucleic acids described in the preceding paragraph operably linked to a promoter.

In yet further embodiments, the invention provides uses of a targeting moiety conjugated or fused to *Pseudomonas* exotoxin A or a cytotoxic fragment or a mutant thereof ("PE"), wherein said PE has a glycine, alanine, valine, leucine, or isoleucine in place of arginine at a position corresponding to position 490 of SEQ ID NO:24, for the manufacture of a medicament to inhibit the growth of cells targeted by said targeting moiety. The PE can be, for example, PE35, PE38, PE38KDEL, PE40, PE4E, or PE38QQR. In some preferred embodiments, the PE has an alanine at a position corresponding to position 490 of SEQ ID NO:24. In some preferred embodiments, the targeting moiety is an antibody. The antibody can be, for example, an scFv, a dsFv, a Fab, or a F(ab')2.

In still further embodiments, the invention provides methods of inhibiting the growth of a cell bearing a target molecule. The methods comprise contacting the cell with a chimeric molecule comprising (a) a targeting moiety that binds to the target molecule, and (b) *Pseudomonas* exotoxin A or a cytotoxic fragment or mutant thereof ("PE"), wherein the PE has a glycine, alanine, valine, leucine, or isoleucine in place of arginine at the position corresponding to position 490 of SEQ ID NO:24, wherein contacting the cell with the chimeric molecule inhibits the growth of said cell. In some embodiments, the target molecule is a cytokine receptor and the targeting moiety is a cytokine which binds to the receptor. In other embodiments, the target molecule is an antigen and the targeting molecule is an antibody which binds to the antigen. In some of these embodiments, the antigen is a tumor associated antigen. In some embodiments, PE has an alanine in place of arginine at the position corresponding to position 490 of SEQ ID NO:24. In some embodiments, the target molecule is the IL-13 receptor and the targeting molecule is IL-13, a mutated IL-13 that retains the ability to bind the IL-13 receptor, a circularly permuted IL-13, or an antibody that specifically binds a chain of the IL-13 receptor.

BRIEF DESCRIPTION OF THE DRAWINGS

FIG. 1 sets forth the nucleotide sequence (SEQ ID NO:1) and amino acid sequence (SEQ ID NO:2) of the variable region of the RFB4 light chain and the nucleotide sequence (SEQ ID NO:3) and amino acid sequence (SEQ ID NO:4) of the variable region of the RFB4 heavy chain. The CDRs assigned using the IMGT program (Lefranc, *Nucl. Acids Res.* 29:207-209, 2001; also found on-line by entering "http://", followed by "imgt.cines.fr") are underlined (While not numbered, CDRs 1, 2 and 3 of each chain are presented within their respective chain in increasing numerical order. For example, CDR2 of the VH chain (SEQ ID NO:14 is the second region underlined in the VH chain). DNA hot spots (A/G-G-C/T-A/T and A-G-C/T) are highlighted.

FIG. 2 is a print out of Entry Number 038145 of the Kabat database showing the nucleic acid (SEQ ID NO:1) and amino acid sequence (SEQ ID NO:2) of the variable region of the RFB4 light chain and the Kabat position numbering corresponding to each amino acid residue.

FIG. 3 is a print out of Entry Number 038146 of the Kabat database showing the nucleic acid (SEQ ID NO:3) and amino acid sequence (SEQ NO:2) of the variable region of the RFB4 heavy chain and the Kabat position numbering corresponding to each amino acid residue.

FIG. 4A. Purified HA22 (R490A) immunotoxin elution profile from Superose-12 gel filtration column chromatography. The numbers at the bottom of (A) are numbers of fractions marked on the chromatogram.

FIGS. 5A and 5B show inhibition of protein synthesis and FIG. 5C shows cell viability on CD22-positive cells contacted with one of three immunotoxin constructs: BL22, HA22, and HA22(R490A). In FIGS. 5A and B, inhibition of protein synthesis was determined as percentage of [$^3$H]leucine incorporation in cells after 20 hr treatment with indicated concentrations of immunotoxins. FIG. 5A: CA-46 cells, FIG. 5B: Daudi cells. Inhibition (50%) of protein synthesis is halfway between the level of incorporation in the absence of toxin and that in the presence of 10 μg/ml of cycloheximide. FIG. 5C: CA-46 cells were incubated with immunotoxin for 40 hr before the WST-8 was added for 4 hr. Formazan production was measured at OD 450 nm and 650 nm. For all three Figures, the symbols are as follows: ○, BL22; □, HA22; and Δ, HA22 (R490A). Triplicate sample values were averaged for each point.

FIG. 8A: On day 6, when tumors>100 mm$^3$ developed, groups of eight or ten mice were either observed (■) or treated with i.v. injections of HA22 (●) or HA22 (R490A) (∇) diluted in 0.2 ml of PBS/0.2% HSA. Therapy was given once every other day (on days 6, 8, and 10; as indicated by the arrows) with 150 μg/kg QOD×3.

DETAILED DESCRIPTION OF THE INVENTION

Introduction

Figure 4:
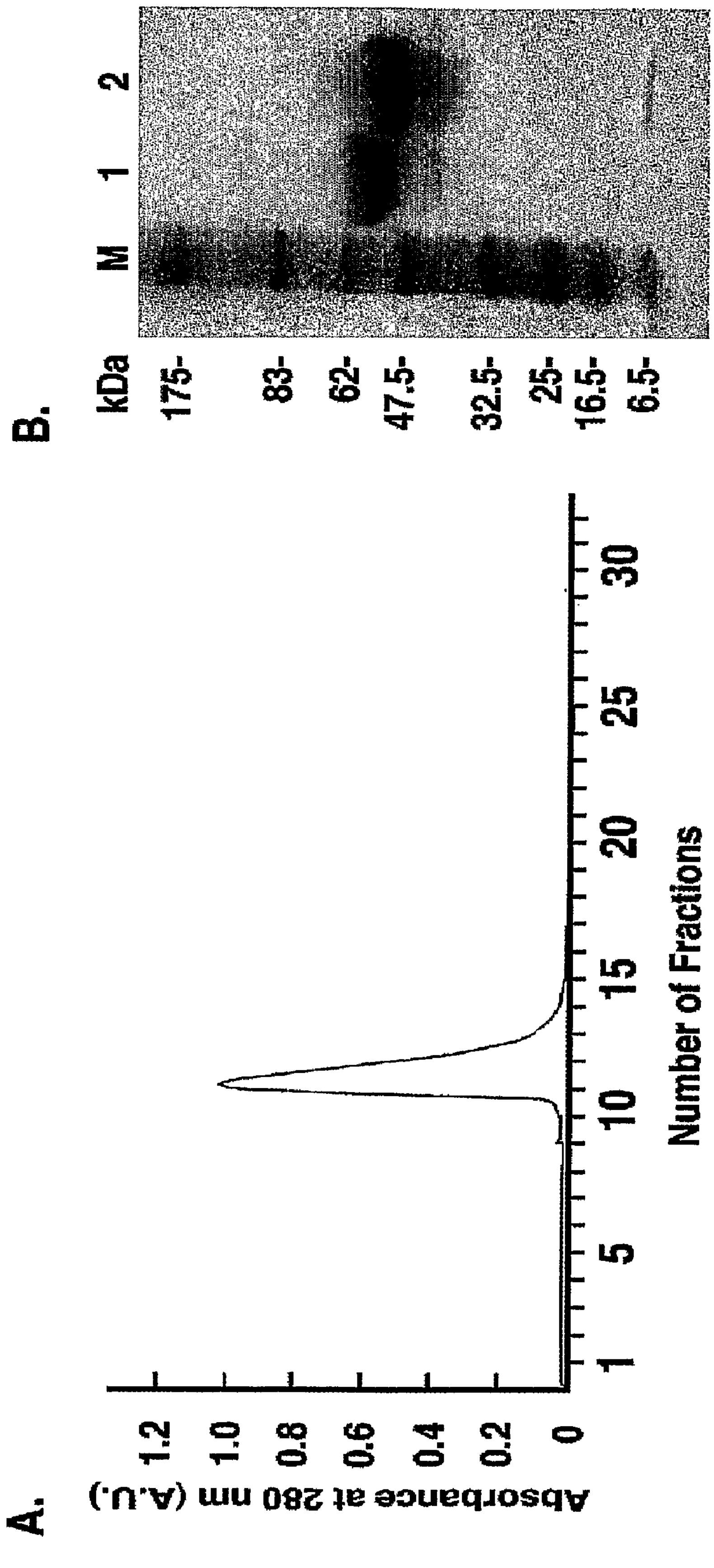
FIGS. 4A and B.
FIG. 4B. SDS-PAGE of HA22 (R490A) under non-reducing and reducing conditions. HA22 (R490A) was prepared as described in Example 2 and elution fraction #12 was analyzed on a 4% to 20% polyacrylamide gel. Lanes: Lane M: molecular weight standards; Lane 1: Non-reducing condition; and Lane 2: The purified HA22 (R490A) immunotoxin was reduced by boiling for 5 min in SDS sample buffer containing DTT. The gel was stained with Coomassie Blue. The nonreduced dsFv immunotoxin migration shows an $M_r$~63,000, Lane 2 shows that it dissociated into a $V_L$ chain ($M_r$~12,000) and a $V_H$-PE38 fusion protein ($M_r$~51,000) under reducing conditions.

A. Discovery of Higher Affinity Anti-CD22 Antibodies

Previous work from the laboratory of the present inventors resulted in the discovery of forms of the anti-CD22 antibody RFB4 that had remarkably increased affinity for CD22. In those studies, the RFB4 antibody was improved by mutating residues in RFB4 VH CDR3 (H-CDR3). See, Salvatore, G., et al., *Clin Cancer Res,* 8(4):995-1002 (2002) and co-owned application PCT/US02/30316, International Publication WO 03/027135. These high affinity mutants of RFB4 were made by mutating the native sequence SSY at positions 100, 100A and 100B of H-CDR3 to one of the following four sequences: THW, YNW, TTW, and STY. The highest affinity mutant was the mutation of SSY to THW. When made into an immunotoxin, an RFB4 dsFv with THW substituted for SSY increased the cytotoxic activity of the immunotoxin to cells of the CD22-bearing cancer chronic lymphocytic leukemia by 50 times compared to the same immunotoxin made with an RFB4 dsFv with the native SSY sequence. For convenience of reference, the term "HA22" will be used below to refer to RFB4 sequences in which the "SSY" of H-CDR3 is mutated to "THW," and at times will specifically refer to the dsFv form fused to a PE38 cytoxotoxin. Which meaning is intended will be clear in context.

Surprisingly, it has now been discovered than even the high affinity antibody HA22 can be improved to provide antibodies and antibody fragments that have increased binding affinity for cancer cells bearing the CD22 antigen compared not only to RFB4 but even when compared to HA22. Moreover, immunotoxins made with the new, higher affinity variants had even greater cytotoxicity than did immunotoxins made with HA22. Thus, in one aspect, the present invention provides important new reagents and agents for detecting and for attacking cancer cells expressing CD22.

The new mutants change the amino acid sequence of the residues at positions 30 and 31 of CDR1 of the $V_L$ chain of RFB4 ("L-CDR1"), as those positions are numbered under the "Kabat and Wu" antibody residue numbering system, from the wild type sequence Serine-Asparagine (in single letter code, "SN") to (a) Histidine-Glycine ("HG," the antibody made by combining an RFB4 light chain containing this L-CDR1 mutant with an RFB4 heavy chain containing the THW H-CDR3 mutant is designated as "B5"), (b) Glycine-Arginine ("GR," the antibody made by combining an RFB4 light chain containing this L-CDR1 mutant with an RFB4 heavy chain containing the THW H-CDR3 mutant is designated as "E6"), (c) Arginine-Glycine ("RG," the antibody made by combining an RFB4 light chain containing this L-CDR1 mutant with an RFB4 heavy chain containing the THW H-CDR3 mutant is designated as "B8"), or (d) Alanine-Arginine ("AR," the antibody made by combining an RFB4 light chain containing this L-CDR1 mutant with an RFB4 heavy chain containing the THW H-CDR3 mutant is designated as "D8").

The amino acid sequence of the RFB4 $V_L$ chain (SEQ ID NO:2), and the Kabat and Wu numbering for each residue in the chain, is shown in FIG. 2 (the Kabat and Wu number for each residue is set forth in the second of the two vertical columns of numbers).

The new mutants were discovered in the course of in vitro affinity maturation studies. Remarkably, some of the best binding mutations resulted from double or even triple mutations in each codon, which rarely happens in somatic hypermutation in B cells. As noted, each of these four mutants had higher affinity for CD22 than did the parental antibody HA22. The order of their relative affinity is, from lowest to highest affinity, B8, D8 and E6 (which are roughly equal), and B5.

Surprisingly, when the THW mutation of the heavy chain CDR3 of RFB4 was combined in an immunotoxin with the newly discovered mutants of the light chain CDR1 of RFB4, the cytotoxicity of the immunotoxins was doubled again over the toxicity of the HA22-based immunotoxin. As shown below in Table 5 of Example 1, in contrast, mutants made by in vitro affinity maturation of CDR1 of the HA22 heavy chain had no effect on the cytotoxicity of immunotoxins made from the resulting mutants, evidencing that not all CDRs can be mutated in ways that improve either affinity of the antibody or of the cytotoxicity of immunotoxins made from the antibodies.

The L-CDR1 mutants set forth above can be substituted into the native sequence of the RFB4 light chain (SEQ ID NO:2), in combination with a RFB4 heavy chain of native sequence (SEQ ID NO:4) to create antibodies of higher affinity for CD22 than parental antibody RFB4. Preferably, the L-CDR1 mutations set forth above are used in a RFB4 light chain in combination with one of the four H-CDR3 mutants described above, in which the native sequence SSY at positions 100, 100A and 100B of H-CDR3 is mutated to one of the following four sequences: THW, YNW, TTW, and STY. More preferably, the L-CDR1 mutants described above are used in a RFB4 light chain in combination with a RFB4 heavy chain in which the native sequence SSY at positions 100, 100A and 100B of H-CDR3 is mutated to THW.

Persons of skill in the art will recognize that it is the complementarity determining regions ("CDRs") that are responsible for an antibody's specificity and affinity, while the framework regions contribute more generally to the 3-dimensional shape and configuration of the molecule and have less impact on the antibody's specificity and affinity. Persons of skill are also aware that, for example, conservative substitutions can typically be made in the framework regions (three of which are present in each variable light and heavy chain), without significantly affecting antigen binding or specificity.

It will therefore be appreciated that changes can be made in the RFB4 antibody, such as changes in the framework region, without significantly affecting the ability of the antibody to bind CD22. Thus, an antibody can readily be engineered comprising one of the L-CDR1 mutants of the invention and not have the precise sequence of the exemplar antibodies discussed herein. Thus, the anti-CD22 antibodies of the invention encompass antibodies that bind CD22 and that comprise one of the L-CDR1 mutants of the invention as the CDR1 of their light chain, whether or not they have the full sequence of the other CDRs or light chain described herein.

The framework regions (non-CDR regions) of the antibodies can be engineered to replace residues found at particular positions in the antibodies of non-human animals, such as mice, with the residues more typically found at the same position in human antibodies. Antibodies engineered in these ways are referred to as "humanized antibodies" and are preferred, since they have a lower risk of inducing side effects and typically can remain in the circulation longer. Methods of humanizing antibodies are known in the art and are set forth in, for example, U.S. Pat. Nos. 6,180,377; 6,407,213; 5,693,762; 5,585,089; and 5,530,101. Further, since the CDRs of the variable regions determine antibody specificity, the CDRs or Fvs described above, can be grafted or engineered into an antibody of choice to confer CD22-specificity upon that antibody. For example, the complementarity determining regions (CDRs), i.e., the antigen binding loops, from an antibody of a non-human animal, such as a mouse, can be grafted onto a human antibody framework of known three dimensional structure (see, e.g., WO98/45322; WO 87/02671; U.S. Pat. No. 5,859,205; U.S. Pat. No. 5,585,089; U.S. Pat. No. 4,816,567; EP Patent Application 0173494; Jones, et al. *Nature* 321:522 (1986); Verhoeyen, et al., *Science* 239:1534 (1988), Riechmann, et al. *Nature* 332:323 (1988); and Winter & Milstein, *Nature* 349:293 (1991)).

In preferred embodiments, the light chain and heavy chain of the variable region are joined by a disulfide bond between cysteines engineered into the framework region, to form a disulfide-stabilized Fv, or "dsFv." Formation of dsFvs is known in the art, and is taught in, for example, Pastan, U.S. Pat. No. 6,558,672, which sets forth a series of positions at which cysteines can be engineered into the framework region to facilitate formation of disulfide bonding between the chains. In a particularly preferred form, the cysteines are engineered into the framework region as the positions used to create RFB4 dsFv. As noted in the Background section, RFB4 dsFv, a dsFv made from the native RFB4 sequence, has been successfully used in clinical trials to direct cytotoxin to cells of a CD22-expressing cancer. The RFB4 dsFv is engineered with a cysteine replacing the glycine at position 100 (as numbered under the Kabat numbering shown in FIG. 2) of the $V_L$ chain and a cysteine replacing the arginine at position 44 (as numbered under the Kabat numbering shown in FIG. 3) of the $V_H$ chain. Materials and methods for constructing the RFB4 dsFv are set forth in, for example, Kreitman et al., Clin. Cancer Res 6:1476-1487 (2000) and Kreitman et al., Intl J Cancer 81:148-155 (1999).

These same methods can be used for generation of the dsFvs of the present, mutated forms of RFB4 of the invention. Typically, the two chains are expressed from separate plasmids in a prokaryotic host cell, such as *E. coli*, and allowed to bond before the protein is purified from the inclusion bodies, as described in the Examples, below.

The improved affinity of the antibodies and antibody fragments provided by the present invention can be incorporated into chimeric immunoconjugates to improve the ability of the chimeric immunoconjugate to target B-cells bearing the CD22 antigen. The immunoconjugates can, for example, bear a detectable label such as a radioisotope, a fluorescent moiety, or a reporter enzyme. These labeled immunoconjugates be used, for example, in in vitro assays to detect the presence of CD22-expressing cells in a biological sample. Typically, the biological sample will be a blood sample or will contain lymphocytes from a blood sample.

In another set of in vitro uses, the immunoconjugate bears a cytotoxin rather than a detectable label. Such immunotoxins can be used to purge a blood sample or culture of lymphocytes from a patient. The purged sample or culture can then be readministered to the patient to boost the functional white-blood cell population.

In in vivo uses, immunotoxins made with the antibodies or antibody fragments of the invention can be used to inhibit the growth and proliferation of cancer cells bearing the CD22 antigen. As noted in the Background section, a clinical trial of an immunotoxin made with the parental antibody, RFB4 in patients with the exemplar CD22-expressing cancer hairy cell leukemia, resulted complete remissions in 86% of the patients. The greater affinity of the antibodies and antibody fragments of the invention compared to the parental RFB4 and HA22 antibodies, and the greater cytotoxicity of the resulting immunotoxins means that smaller amounts of the immunotoxins can be administered, thereby achieving the same therapeutic effect while reducing the chance of side effects.

In preferred embodiments, the antibody is a scFv or a dsFv. Many of the recombinant immunotoxins produced from constructs of scFv are one-third the size of IgG-toxin chemical conjugates and are homogeneous in composition. Elimination of the constant portion of the IgG molecule from the scFv results in faster clearance of the immunotoxin after injection into animals, including primates, and the smaller size of the conjugates improves drug penetration in solid tumors. Together, these properties lessen the side effects associated with the toxic moiety by reducing the time in which the immunotoxin (IT) interacts with non-target tissues and tissues that express very low levels of antigen. Making disulfide stabilized Fvs (dsFvs) from anti-CD22 antibodies is discussed above and in the co-owned application of FitzGerald et al., International Publication Number WO 98/41641, which is incorporated herein by reference.

These advantages, however, are offset to some degree by the loss of antigen binding affinity that occurs when IgGs are converted to scFvs (Reiter et al., Nature Biotechnol. 14:239-1245 (1996)). Increasing affinity has been shown to improve selective tumor delivery of scFvs (Adams et al., Cancer Res. 58:485-490 (1998)), and is likely to increase their usefulness in tumor imaging and treatment. Therefore, increasing the affinity of scFvs and other targeting moieties (such as dsFvs, Fabs. and F(ab')2 of immunoconjugates is desirable to improve the efficiency of these agents in delivering effector molecules, such as toxins and other therapeutic agents, to their intended targets. The improved affinity of the antibodies of the invention therefore is an important advance in the delivery of toxins, drugs, and other therapeutic agents to cell of CD22-expressing cancers.

B. Discovery of More Cytotoxic Form of *Pseudomonas* Exotoxin A

For some 15 years, *Pseudomonas* exotoxin A ("PE") has been investigated as the toxic portion of chimeric molecules, such as immunotoxins. That work is embodied in the development of a number of mutated forms of PE in which cytotoxic activity has been retained, while the non-specific toxicity of the molecule has been reduced or eliminated. Most of these mutants are truncated, which improves their tumor penetration. Some of these mutants have also had modifications, such as modifying the carboxyl terminal residues, or eliminating the requirement for cleavage between residues 279 and 280 by the protease furin, that have increased cytotoxicity or activity.

Surprisingly, it has now been discovered that the toxicity of PE can be doubled by a single amino acid substitution in the molecule. The mutation can easily be engineered into the various forms of modified PEs previously developed in the art (such as PE40, PE38, PE37, PE35, PE4E, PE38QQR, and PE38KDEL) to increase their potency and activity. It is expected that this will permit reducing the dose of PE-based immunotoxins required to produce a desired clinical result, which should reduce the possibility of undesirable side effects. Conversely, the same dose of PE-based immunotoxin can be administered, but with more potent effect. Accordingly, the invention provides an important new means to increase the potency of PE-based immunoconjugates, such as the RFB4 dsFv-PE constructs currently in clinical trials and constructs made with the various mutants of RFB4 set forth above.

The improved PEs of the invention comprise mutations of the arginine (R) at position 490 of the PE molecule (by convention, positions in PE and its variants are described by reference to the sequence of the native PE molecule. The 613-amino acid sequence of native PE is well known in the art and is set forth, for example, as SEQ ID NO:1 of U.S. Pat. No. 5,602,095). The R is mutated to an amino acid having an aliphatic side chain that does not comprise a hydroxyl. Thus, the R can be mutated to glycine (G), alanine (A), valine (V), leucine (L), or isoleucine (I). In preferred embodiments, the substituent is G, A, or I. Alanine is the most preferred.

Comparisons of the HA22 immunotoxin to a like immunotoxin made with the R490A mutation ("HA22 R490A" showed that the HA22 R490A immunotoxin had two to three times the cytotoxicity to target cells of the HA22 immunotoxin. See, Example 3. Moreover, comparisons were made comparing the effect of HA22 R490A and HA22 on animals bearing xenografts of CD22-expressing human tumors. Markedly greater reductions in tumor mass were seen in animals treated with HA22 R490A than in animals undergoing identical treatment with the same immunotoxin made without the R490A mutation. See, Example 4.

The change in cytotoxicity is all the more surprising given that mutants previously made which encompass substitutions at the same position changed the molecule's half life in the circulation, but did not change the cytotoxicity. See, Brinkmann et al., Proc Natl Acad Sci, USA 89:3065-3069 (1992). The PE mutants of the present invention exhibit a slightly shortened half life in the circulation compared to like PE constructs that do not contain the mutation at position 490. Given the significant reduction of tumor mass in animals treated with an immunotoxin with the R490A mutant compared to animals treated with the same amount of the same immunotoxin made without the R490A mutation, however, it is apparent that the increased cytotoxicity of the PE molecule outweighs the small decrease in half life.

Studies were undertaken to confirm that the results seen with HA22 were generally applicable to PE-based immunotoxins. Mesothelin is an antigen that is highly expressed on pancreatic and ovarian cancers and mesotheliomas. SS1 is an antibody with high affinity for mesothelin, as described in co-owned international application PCT/US00/14829, published as WO 00/73346. SS1P is an SS1-PE immunotoxin that binds to mesothelin and kills mesothelin expressing cells. As reported in Example 5, SS1P made with the R490A mutation was twice as cytotoxic to mesothelin-expressing cell lines as was SS1P itself.

Thus, mutations of R490 as taught herein can be used to confer increased cytotoxicity to chimeric molecules using PE and its derivatives as the toxic moiety. Persons of skill are aware that various types of molecules can serve as a basis of targeting cells that the practitioner wishes to kill or to inhibit. As evident from the discussion above, antibodies are one especially preferred type of targeting agent. Chimeric molecules of antibodies attached to a PE of the invention are particularly useful for inhibiting the growth of cancer cells bearing tumor associated antigens. A large number of tumor associated antigens are known in the art, including, for example, the melanoma antigens MART-1, gp100, and MAGE-1, the colon cancer antigen "CEA" (carcino embryonic antigen), the breast cancer antigen HER-2, the lung cancer antigen L6 (Kao et al., Clin Cancer Res. 9(7):2807-16 (2003)), the ovarian cancer antigen CA125, and, of course, mesothelin. As is well known in the art, antigens which remain accessible on the cell surface are preferred as targets, since binding of the chimeric molecule to them permits entry of the PE into the cell, resulting in cell death.

In another preferred embodiment, the targeting portion, or moiety, of the chimeric molecule is a cytokine, which can be used to target toxins to cells overexpressing a receptor for the cytokine, or an antibody to the receptor. For example, IL-13 receptors are known to be heavily overexpressed on the exterior of cells of certain cancers, such as gliomas, and to act as an autocrine growth factor on such cancers as renal cell carcinoma, Kaposi's sarcoma, and Hodgkin's disease. See, e.g., WO 01/34645, WO 03/039600 and U.S. Pat. No. 6,518,061. IL-13 or various mutants and circularly permuted forms of IL-13 can be used as the targeting portion of cytotoxins, such as PE molecules containing a R490 mutation to an aliphatic amino acid that does not contain a hydroxyl group in the side chain, to cells expressing the IL-13 receptor. Similarly, the IL-13 receptor can be targeted by antibodies to the IL-13 receptor. Antibodies specific for the IL-13 receptor that do not also bind the IL-4 are also suitable for use in such methods. As is known in the art, for example, the IL-13Rα2 is not implicated in complexes which also bind IL-4. Thus, the human IL-13Rα chain can be expressed and antibodies raised against it, or DNA encoding the chain can be injected into mice so that it is expressed in the mice and antibodies raised. It should be noted that the IL-4 receptor has been cloned. Thus, any particular antibody raised against the IL-13 receptor can be readily tested to see if it binds IL-4 receptor by simple tests, such as by running the IL-13 receptor antibody through a column holding immobilized IL-4 receptor.

Further, the various forms of IL-13, including circularly permuted forms, and antibodies to the receptor, can be used to target PE molecules with the R490 mutations to cells in the lungs expressing IL-13 receptor to reduce or end symptoms in conditions mediated or aggravated by IL-13, such as asthma and allergic rhinitis, and to cells elsewhere in the body to reduce or end symptoms of atopic dermatitis, and hepatic fibrosis in schistosomiasis, as discussed in International Publication WO 01/34645.

In addition to cytokines, numerous other ligands are known in the art and can be used for targeting PE molecules of the invention to target cells. For example, transferrin has been used as a means of targeting toxins to cells expressing transferrin receptors. Any cell involved in a disease can be targeted if there is an antigen on the cell surface that is specifically expressed, e.g., gp 120 in HIV-infected cells, CD25 on T cells that are involved in graft versus host disease or various surface molecules that are expressed on cancer cells, such as CEA, CD30, or CD33.

DEFINITIONS

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

"CD22" refers to a lineage-restricted B cell antigen belonging to the Ig superfamily. It is expressed in 60-70% of B cell lymphomas and leukemias and is not present on the cell surface in early stages of B cell development or on stem cells. See, e.g. Vaickus et al., Crit. Rev. Oncol/Hematol. 11:267-297 (1991).

As used herein, the term "anti-CD22" in reference to an antibody, refers to an antibody that specifically binds CD22 and includes reference to an antibody which is generated against CD22. In preferred embodiments, the CD22 is a primate CD22 such as human CD22. In one preferred embodiment, the antibody is generated against human CD22 synthesized by a non-primate mammal after introduction into the animal of cDNA which encodes human CD22.

"RFB4" refers to a mouse IgG1 monoclonal antibody that specifically binds to human CD22. RFB4 is commercially available under the name RFB4 from several sources, such as Southern Biotechnology Associates, Inc. (Birmingham Ala.; Cat. No. 9360-01), Autogen Bioclear UK Ltd. (Caine, Wilts, UK; Cat. No. AB147), Axxora LLC. (San Diego, Calif.). RFB4 is highly specific for cells of the B lineage and has no detectable cross-reactivity with other normal cell types. Li et al., Cell. Immunol. 118:85-99 (1989). The heavy and light chains of RFB4 have been cloned. See, Mansfield et al., Blood 90:2020-2026 (1997), which is incorporated herein by reference. The nucleotide sequence and amino acid sequences of the RFB4 light chain are SEQ ID NO:1 and SEQ ID NO:2, respectively. The nucleotide sequence and amino acid sequences of the RFB4 heavy chain are SEQ ID NO:3 and SEQ ID NO:4, respectively. The sequences of each chain are set forth in FIG. 1.

The positions of the CDRs and framework regions of RFB4 can be determined using various well known definitions in the art, e.g., Kabat, Chothia, the international ImMunoGeneTics database ("IMGT" available on the World Wide Web at ebi-.ac.uk/imgt/), and AbM (see, e.g., Chothia & Lesk, "Canonical structures for the hypervariable regions of immunoglobulins," *J. Mol. Biol.* 196:901-917 (1987); Chothia C. et al., "Conformations of immunoglobulin hypervariable regions," Nature 342:877-883 (1989); Chothia C. et al., "Structural repertoire of the human VH segments," J. Mol. Biol. 227:799-817 (1992). Definitions of antigen combining sites are also described in the following: Ruiz et al., "IMGT, the international ImMunoGeneTics database," *Nucleic Acids Res.,* 28:219-221 (2000); and Lefranc, M.-P. "IMGT, the international ImMunoGeneTics database," *Nucleic Acids Res.* January 1; 29(1):207-9 (2001); MacCallum et al, "Antibody-antigen interactions: Contact analysis and binding site topography," *J. Mol. Biol.,* 262 (5):732-745 (1996); Martin et al, *Proc. Natl Acad. Sci. USA,* 86:9268-9272 (1989); Martin, et al, *Methods Enzymol.,* 203:121-153, (1991); Pedersen et al, *Immunomethods,* 1: 126, (1992); and Rees et al, In Sternberg M. J. E. (ed.), Protein Structure Prediction. Oxford University Press, Oxford, 141-172 (1996).

Unless otherwise indicated, references herein to amino acid positions of the RFB4 heavy or light chain refer to the numbering of the amino acids under the "Kabat and Wu" system, which is the most widely used antibody numbering systems. See, Kabat, E., et al., SEQUENCES OF PROTEINS OF IMMUNOLOGICAL INTEREST, U.S. Government Printing Office, NIH Publication No. 91-3242 (1991), which is hereby incorporated by reference. The Chothia number scheme is identical to the Kabat scheme, but places the insertions in CDR-L1 and CDR-H1 at structurally different positions. It should be noted that the number accorded to a residue under the Kabat and Wu system does not necessarily correspond to the number that one might obtain for a residue in a given heavy or light chain by counting from the amino terminus of that chain. Thus, the position of an amino acid residue in a particular $V_H$ or $V_L$ sequence does not refer to the number of amino acids in a particular sequence, but rather refers to the position as designated with reference to the Kabat numbering scheme. FIGS. 2 and 3 show the correlation between the sequential numbering of the residues of the RFB4 light and heavy chains and the Kabat and Wu numbering of those residues. For convenience, the "Kabat and Wu" numbering is sometimes referred to herein as "Kabat" numbering.

Mutations are described herein in conventional notation. Thus, for example, the term "R490A" indicates that the "R"

(arginine, in standard single letter code) at position 490 of the referenced molecule is replaced by an "A" (alanine, in standard single letter code). The standard single letter code for common amino acids is set forth below.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies), heteroconjugate antibodies (e.g., bispecific antibodies), recombinant single chain Fv fragments (scFv), and disulfide stabilized (dsFv) Fv fragments (see, co-owned U.S. Pat. No. 5,747,654, which is incorporated herein by reference). The term "antibody" also includes antigen binding forms of antibodies (e.g., Fab', $F(ab')_2$, Fab, Fv and rIgG. See also, Pierce Catalog and Handbook, 1994-1995 (Pierce Chemical Co., Rockford, Ill.); Goldsby et al., eds., Kuby, J., *Immunology,* 4th Ed., W.H. Freeman & Co., New York (2000).

An antibody immunologically reactive with a particular antigen can be generated by recombinant methods such as selection of libraries of recombinant antibodies in phage or similar vectors, see, e.g., Huse, et al., *Science* 246:1275-1281 (1989); Ward, et al., *Nature* 341:544-546 (1989); and Vaughan, et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. See, Kabat and Wu, supra. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain, including an Fv, scFv, dsFv or Fab. References to "$V_L$" or a "VL" refer to the variable region of an immunoglobulin light chain, including of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond.

The phrase "disulfide stabilized Fv" or "dsFv" refer to the variable region of an immunoglobulin in which there is a disulfide bond between the light chain and the heavy chain. In the context of this invention, the cysteines which form the disulfide bond are within the framework regions of the antibody chains and serve to stabilize the conformation of the antibody. Typically, the antibody is engineered to introduce cysteines in the framework region at positions where the substitution will not interfere with antigen binding.

The term "linker peptide" includes reference to a peptide within an antibody binding fragment (e.g., Fv fragment) which serves to indirectly bond the variable domain of the heavy chain to the variable domain of the light chain.

The term "parental antibody" means any antibody of interest which is to be mutated or varied to obtain antibodies or fragments thereof which bind to the same epitope as the parental antibody, but with higher affinity.

The term "hotspot" means a portion of a nucleotide sequence of a CDR or of a framework region of a variable domain which is a site of particularly high natural variation. Although CDRs are themselves considered to be regions of hypervariability, it has been learned that mutations are not evenly distributed throughout the CDRs. Particular sites, or hotspots, have been identified as these locations which undergo concentrated mutations. The hotspots are characterized by a number of structural features and sequences. These "hotspot motifs" can be used to identify hotspots. Two consensus sequences motifs which are especially well characterized are the tetranucleotide sequence RGYW and the serine sequence AGY, where R is A or G, Y is C or T, and W is A or T.

An "immunoconjugate" is a molecule comprised of a targeting portion, or moiety, such as an antibody or fragment thereof which retains antigen recognition capability, and an effector molecule, such as a therapeutic moiety or a detectable label.

An "immunotoxin" is an immunoconjugate in which the therapeutic moiety is a cytotoxin.

A "targeting moiety" is the portion of an immunoconjugate intended to target the immunoconjugate to a cell of interest. Typically, the targeting moiety is an antibody, a scFv, a dsFv, an Fab, or an $F(ab')_2$.

A "toxic moiety" is the portion of a immunotoxin which renders the immunotoxin cytotoxic to cells of interest.

A "therapeutic moiety" is the portion of an immunoconjugate intended to act as a therapeutic agent.

The term "therapeutic agent" includes any number of compounds currently known or later developed to act as anti-neoplastics, anti-inflammatories, cytokines, anti-infectives, enzyme activators or inhibitors, allosteric modifiers, antibiotics or other agents administered to induce a desired therapeutic effect in a patient. The therapeutic agent may also be a toxin or a radioisotope, where the therapeutic effect intended is, for example, the killing of a cancer cell.

A "detectable label" means, with respect to an immunoconjugate, a portion of the immunoconjugate which has a property rendering its presence detectable. For example, the immunoconjugate may be labeled with a radioactive isotope which permits cells in which the immunoconjugate is present to be detected in inununohistochemical assays.

The term "effector moiety" means the portion of an immunoconjugate intended to have an effect on a cell targeted by the targeting moiety or to identify the presence of the immunoconjugate. Thus, the effector moiety can be, for example, a therapeutic moiety, a toxin, a radiolabel, or a fluorescent label.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "toxin" includes reference to abrin, ricin, *Pseudomonas* exotoxin A (or "PE"), diphtheria toxin ("DT"), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody.

As indicated by the preceding paragraph, the term *Pseudomonas* exotoxin A ("PE") as used herein includes reference to forms of PE which have been modified but which retain cytotoxic function. Thus, the PE molecule can be truncated to provide a fragment of PE which is cytotoxic but which does not bind cells, as in the fragments known as PE38 and PE40, or can have mutations which reduce non-specific binding, as in the version called "PE4E", in which four residues are mutated to glutamic acid. Further, a portion of the PE sequence can be altered to increase toxicity, as in the form called "PE38KDEL", in which the C-terminal sequence of native PE is altered, or the form of PE discussed herein, in which the arginine corresponding to position 490 of the native PE sequence is replaced by alanine, glycine, valine, leucine, or isoleucine.

The term "contacting" includes reference to placement in direct physical association.

An "expression plasmid" comprises a nucleotide sequence encoding a molecule or interest, which is operably linked to a promoter.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |

TABLE A-continued

Amino Acid Nomenclature

| Name | 3-letter | 1-letter |
|---|---|---|
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B each contain amino acids that are conservative substitutions for one another:

TABLE B

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, PROTEINS, W.H. Freeman and Company, New York (1984).

The terms "substantially similar" in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Nat'l Acad. Sci. USA* 82:2306-2309 (1985), or the ciliate *Macronucleus*, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. The phage display the foreign protein encoded by the cDNA on its surface. After replication in a bacterial host, typically *E. coli*, the phage which contain the foreign cDNA of interest are selected by the expression of the foreign protein on the phage surface.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, more preferably 65%, even more preferably 70%, still more preferably 75%, even more preferably 80%, and most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (on the Web at "ncbi.nlm.nih.gov/"). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, preferably greater than 5-fold, more preferably greater than 10-fold and most preferably greater than 100-fold increase in amount of bound antibody (per unit time) to a cell or tissue bearing CD22 as compared to a cell or tissue lacking CD22. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Numbering of Amino Acid Residues in the RFB4 Heavy and Light Chains

The positions of amino acid residues in an antibody heavy chain or light chain are conveniently referred to in the art by standard numbering as set forth in Kabat, E., et al., Sequences of Proteins of Immunological Interest, U.S. Government Printing Office, NIH Publication No. 91-3242 (1991). See also, Johnson, G. and Wu, T., Nuc. Acids Res. 29:205-206 (2001). The Kabat et al. database is typically referred to in the art as either "Kabat" or "Kabat and Wu". The database is currently maintained on-line as a subscription service and can be found by entering "www." followed by "kabatdatabase.com". The heavy and light chains of RFB4 have been cloned. See, Mansfield et al., Blood 90:2020-2026 (1997). The amino acid sequences of the RFB4 $V_L$ and $V_H$ chains and a list of the Kabat numbering of the position of each amino acid residue are set forth in the Kabat database under Entry Numbers 038145 and 038146, respectively. FIG. 2 shows the comparison of the numbering of the amino acids of the RFB4 $V_L$ chain (SEQ ID NO:2) to the corresponding Kabat positions as set forth in Kabat Entry 038145; FIG. 3 shows the same comparison for the amino acids of the RFB4 $V_H$ chain (SEQ ID NO:4), as set forth in Kabat Entry 038146.

Binding of Antibodies and Immunoassays

A. Binding Affinity of Antibodies

The antibodies of this invention bind to their target antigens with an affinity better than that of the parental antibodies RFB4 and BL22. The antibodies are anti-CD22 antibodies which bind to an extracellular epitope of CD22. Binding affinity for a target antigen is typically measured or determined by standard antibody-antigen assays, such as competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($K_D$=1/K, where K is the affinity constant) of the antibody is <1 μM, preferably <100 nM, and most preferably <0.1 nM. Antibody molecules will typically have a $K_D$ in the lower ranges. $K_D$=[Ab-Ag]/[Ab][Ag] where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible noncovalent associations such as electrostatic attraction, Van der Waals forces and hydrogen bonds. This method of defining binding specificity applies to single heavy and/or light chains, CDRs, fusion proteins or fragments of heavy and/or light chains, that are specific for CD22 if they bind CD22 alone or in combination.

B. Immunoassays

Antibodies of the invention can be detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37, Asai, ed. Academic Press, Inc. New York (1993); Basic and Clinical Immunology 7th Edition, Stites & Terr, eds. (1991). Immunological binding assays (or immunoassays) typically utilize a ligand (e.g., CD22) to specifically bind to and often immobilize an antibody. The antibodies employed in immunoassays of the present invention are discussed in greater detail supra.

Immunoassays also often utilize a labeling agent to specifically bind to and label the binding complex formed by the ligand and the antibody. The labeling agent may itself be one of the moieties comprising the antibody/analyte complex, i.e., the anti-CD22 antibody. Alternatively, the labeling agent may be a third moiety, such as another antibody, that specifically binds to the antibody/CD22 protein complex.

In one aspect, a competitive assay is contemplated wherein the labeling agent is a second anti-CD22 antibody bearing a label. The two antibodies then compete for binding to the immobilized CD22. Alternatively, in a non-competitive format, the CD22 antibody lacks a label, but a second antibody specific to antibodies of the species from which the anti-CD22 antibody is derived, e.g., murine, and which binds the anti-CD22 antibody, is labeled.

Other proteins capable of specifically binding immunoglobulin constant regions, such as Protein A or Protein G may also be used as the label agent. These proteins are normal constituents of the cell walls of streptococcal bacteria. They exhibit a strong non-immunogenic reactivity with immunoglobulin constant regions from a variety of species (see, generally Kronval, et al., *J. Immunol.* 111:1401-1406 (1973); and Akerstrom, et al., *J. Immunol.* 135:2589-2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antibody, volume of solution, concentrations, and the like. Usually, the assays will be carried out at ambient temperature, although they can be conducted over a range of temperatures, such as 10° C. to 40° C.

While the details of the immunoassays may vary with the particular format employed, the method of detecting anti-CD22 antibodies in a sample containing the antibodies generally comprises the steps of contacting the sample with an antibody which specifically reacts, under immunologically reactive conditions, to the CD22/antibody complex.

Production of Immunoconjugates

Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents may include various drugs such as vinblastine, daunomycin and the like, cytotoxins such as native or modified *Pseudomonas* exotoxin or Diphtheria toxin, encapsulating agents, (e.g., liposomes) which themselves contain pharmacological compositions, radioactive agents such as $^{125}I$, $^{32}P$, $^{14}C$, $^{3}H$ and 35S and other labels, target moieties and ligands.

The choice of a particular therapeutic agent depends on the particular target molecule or cell and the biological effect is desired to evoke. Thus, for example, the therapeutic agent may be a cytotoxin which is used to bring about the death of a particular target cell. Conversely, where it is merely desired to invoke a non-lethal biological response, the therapeutic agent may be conjugated to a non-lethal pharmacological agent or a liposome containing a non-lethal pharmacological agent.

With the therapeutic agents and antibodies herein provided, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

A. Recombinant Methods

The nucleic acid sequences of the present invention can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., Molecular Cloning: A Laboratory Manual (2nd Ed.), Vols. 1-3, Cold Spring Harbor Laboratory (1989)), Berger and Kimmel (eds.), Guide to Molecular Cloning Techniques, Academic Press, Inc., San Diego Calif. (1987)), or Ausubel, et al. (eds.), Current Protocols in Molecular Biology, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding native EM or anti-CD22 antibodies can be modified to form the EM, antibodies, or immunoconjugates of the present invention. Modification by site-directed mutagenesis is well known in the art. Nucleic acids encoding EM or anti-CD22 antibodies can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an anti-CD22 scFv antibody into a vector which comprises the cDNA encoding the EM. The insertion is made so that the scFv and the EM are read in frame, that is in one continuous polypeptide which contains a functional Fv region and a functional EM region. In a particularly preferred embodiment, cDNA encoding a diphtheria toxin fragment is ligated to a scFv so that the toxin is located at the carboxyl terminus of the scFv. In more preferred embodiments, cDNA encoding PE is ligated to a scFv so that the toxin is located at the amino terminus of the scFv.

Once the nucleic acids encoding an EM, anti-CD22 antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli* other bacterial hosts, yeast, and various higher eukaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., anti-CD22 antibody, PE, or an immunoconjugate formed from their combination) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

In addition to recombinant methods, the immunoconjugates, EM, and antibodies of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield, et al. *J. Am. Chem. Soc.* 85:2149-2156 (1963), and Stewart, et al., Solid Phase Peptide Synthesis, 2nd ed., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N, N'-dicycylohexylcarbodiimide) are known to those of skill.

B. Purification

Once expressed, the recombinant immunoconjugates, antibodies, and/or effector molecules of the present invention can be purified according to standard procedures of the art, including ammonium sulfate precipitation, affinity columns, column chromatography, and the like (see, generally, R. Scopes, Protein Purification, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies of this invention. See, Buchner, et al., *Anal. Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

*Pseudomonas* Exotoxin and Other Toxins

Toxins can be employed with antibodies of the present invention to yield immunotoxins. Exemplary toxins include ricin, abrin, diphtheria toxin and subunits thereof, as well as botulinum toxins A through F. These toxins are readily available from commercial sources (e.g., Sigma Chemical Company, St. Louis, Mo.). Diphtheria toxin is isolated from *Corynebacterium diphtheriae*. Ricin is the lectin RCA60 from *Ricinus communis* (Castor bean). The term also references toxic variants thereof. For example, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543 (1972)). The A chain is responsible for inactivating protein synthesis and killing cells. The B chain binds ricin to cell-surface galactose residues and facilitates transport of the A chain into the cytosol (Olsnes, et al, *Nature* 249:627-631 (1974) and U.S. Pat. No. 3,060,165).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095 (1988); and Olsnes, *Methods Enzymol.* 50:330-335 (1978)).

In preferred embodiments of the present invention, the toxin is *Pseudomonas* exotoxin A ("PE"). Native *Pseudoinonas* exotoxin A (PE) is an extremely active monomeric protein (molecular weight 66 kD), secreted by *Pseudomonas aeruginosa*, which inhibits protein synthesis in eukaryotic cells. The native PE sequence is set forth in SEQ ID NO:1 of U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall, et al., J Biol Chem 264:14256-61 (1989).

The terms "*Pseudomonas* exotoxin" and "PE" as used herein typically refer to a PE that has been modified from the native protein to reduce or to eliminate non-specific toxicity. Such modifications may include, but are not limited to, elimination of domain Ia, various amino acid deletions in domains Ib, II and III, single amino acid substitutions and the addition of one or more sequences at the carboxyl terminus such as KDEL (SEQ ID NO:5) and REDL (SEQ ID NO:6). See Siegall, et al., *J. Biol. Chem.* 264:14256-14261 (1989). Cytotoxic fragments of PE include those which are cytotoxic with or without subsequent proteolytic or other processing in the target cell (e.g., as a protein or pre-protein). Cytotoxic fragments of PE include PE40, PE38 and its variants PE38QQR and PE38KDEL, and PE35, as discussed below. In a preferred embodiment, the cytotoxic fragment of PE retains at least 50%, preferably 75%, more preferably at least 90%, and most preferably 95% of the cytotoxicity of native PE. In a most preferred embodiment, the cytotoxic fragment is more toxic than native PE.

In preferred embodiments, the PE has been modified to reduce or eliminate non-specific cell binding, frequently by deleting domain Ia. as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as PE4E.

PE40 is a truncated derivative of PE as previously described in the art. See, Pai, et al., *Proc. Nat'l Acad. Sci. USA* 88:3358-62 (1991); and Kondo, et al., *J. Biol. Chem.* 263: 9470-9475 (1988). PE35 is a 35 kD carboxyl-terminal fragment of PE in which amino acid residues 1-279 have deleted and the molecule commences with a met at position 280 followed by amino acids 281-364 and 381-613 of native PE. PE35 and PE40 are disclosed, for example, in U.S. Pat. Nos. 5,602,095 and 4,892,827.

In some preferred embodiments, the cytotoxic fragment PE38 is employed. PE38 contains the translocating and ADP ribosylating domains of PE but not the cell-binding portion (Hwang, J. et al., *Cell,* 48:129-136 (1987)). PE38 is a truncated PE pro-protein composed of amino acids 253-364 and 381-613 which is activated to its cytotoxic form upon processing within a cell (see e.g., U.S. Pat. No. 5,608,039, and Pastan et al., Biochim. Biophys. Acta 1333:C1-C6 (1997)). The sequence of PE38 can be readily determined by the practitioner from the known sequence of PE, but for convenience, it is also set forth as SEQ ID NO:22. Persons of skill will be aware that, due to the degeneracy of the genetic code, the amino acid sequence of PE38, of its variants, such as PE38KDEL, and of the other PE derivatives discussed herein can be encoded by a great variety of nucleic acid sequences, any of which can be expressed to result in the desired polypeptide.

As noted above, some or all of domain 1b may be deleted, and the remaining portions joined by a linker or directly by a peptide bond. Some of the amino portion of domain II may be deleted. And, the C-terminal end may contain the native sequence of residues 609-613 (REDLK (SEQ ID NO:30)), or may contain a variation found to maintain the ability of the construct to translocate into the cytosol, such as REDL (SEQ ID NO:6) or KDEL (SEQ ID NO:5), and repeats of these sequences. See, e.g., U.S. Pat. Nos. 5,854,044; 5,821,238; and 5,602,095 and WO 99/51643. While in preferred embodiments, the PE is PE4E, PE40, or PE38, any form of PE in which non-specific cytotoxicity has been eliminated or reduced to levels in which significant toxicity to non-targeted cells does not occur can be used in the immunotoxins of the present invention so long as it remains capable of translocation and EF-2 ribosylation in a targeted cell.

In preferred embodiments, the PE molecules are further modified to have a substitution of an aliphatic amino acid in place of the arginine normally present at position 490 of the PE molecule. The substitute amino acids can be, for example, G, A, V, L, or I. G, A, and I are more preferred substitutes, with A being the most preferred. Thus, for example, PE40, PE38, PE38KDEL, PE38QQR, PE4E, PE37, or PE35 can be engineered to have a G, A, or I at position 490 to improve the cytotoxicity of the molecule. In particularly preferred embodiments, the residue at position 490 is changed to an alanine. An exemplar sequence, with the R at position 490 of PE38 mutated to alanine, is set forth as SEQ ID NO:23.

A. Conservatively Modified Variants of PE

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

B. Assaying for Cytotoxicity of PE

*Pseudomonas* exotoxins employed in the invention can be assayed for the desired level of cytotoxicity by assays well known to those of skill in the art. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE.

C. Other Therapeutic Moieties

Antibodies of the present invention can also be used to target any number of different diagnostic or therapeutic compounds to cells expressing CD22 on their surface. Thus, an antibody of the present invention, such as an anti-CD22 scFv, may be attached directly or via a linker to a drug that is to be delivered directly to cells bearing CD22. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-CD22 antibody may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735; and Connor, et al., *Pharm. Ther.* 28:341-365 (1985).

D. Detectable Labels

Antibodies of the present invention may optionally be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

E. Conjugation to the Antibody

In a non-recombinant embodiment of the invention, effector molecules, e.g., therapeutic, diagnostic, or detection moieties, are linked to the anti-CD22 antibodies of the present invention using any number of means known to those of skill in the art. Both covalent and noncovalent attachment means may be used with anti-CD22 antibodies of the present invention.

The procedure for attaching an effector molecule to an antibody will vary according to the chemical structure of the EM. Polypeptides typically contain a variety of functional groups; e.g., carboxylic acid (COOH), free amine (—$NH_2$) or sulfhydryl (—SH) groups, which are available for reaction with a suitable functional group on an antibody to result in the binding of the effector molecule.

Alternatively, the antibody is derivatized to expose or to attach additional reactive functional groups. The derivatization may involve attachment of any of a number of linker molecules such as those available from Pierce Chemical Company, Rockford Ill.

A "linker", as used herein, is a molecule that is used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages which are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

Pharmaceutical Compositions and Administration

The antibody and/or immunoconjugate compositions of this invention (i.e., PE linked to an anti-CD22 antibody of the invention) are particularly useful for parenteral administration, such as intravenous administration or administration into a body cavity.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunotoxin composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp.315-339, (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., *Accounts Chem. Res.* 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., *Pharm. Res.* 9:425-434 (1992); and Pec, et al., *J. Parent. Sci. Tech.* 44(2):58-65 (1990)). Alternatively, hydroxyapatite has been used as a microcarrier for controlled release of proteins (Ijntema, et al, *Int. J. Pharm.* 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins of the present invention are included a variety of disease conditions caused by specific human cells that may be eliminated by the toxic action of the fusion protein. One preferred application for the immunotoxins of the invention is the treatment of malignant cells expressing CD22. Exemplary malignant cells include those of chronic lymphocytic leukemia and hairy cell leukemia.

Diagnostic Kits and In Vitro Uses

In another embodiment, this invention provides for kits for the detection of CD22 or an immunoreactive fragment thereof, (i.e., collectively, a "CD22 protein") in a biological sample. A "biological sample" as used herein is a sample of biological tissue or fluid that contains CD22. Such samples include, but are not limited to, tissue from biopsy, blood, and blood cells (e.g., white cells). Preferably, the cells are lymphocytes. Biological samples also include sections of tissues, such as frozen sections taken for histological purposes. A biological sample is typically obtained from a multicellular eukaryote, preferably a mammal such as rat, mouse, cow, dog, guinea pig, or rabbit, and more preferably a primate, such as a macaque, chimpanzee, or human. Most preferably, the sample is from a human.

Kits will typically comprise an anti-CD22 antibody of the present invention. In some embodiments, the anti-CD22 antibody will be an anti-CD22 Fv fragment, such as a scFv or dsfv fragment.

In addition the kits will typically include instructional materials disclosing means of use of an antibody of the present invention (e.g. for detection of mesothelial cells in a sample). The kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In one embodiment of the present invention, the diagnostic kit comprises an immunoassay. As described above, although the details of the immunoassays of the present invention may vary with the particular format employed, the method of detecting CD22 in a biological sample generally comprises the steps of contacting the biological sample with an antibody of the present invention which specifically reacts, under immunologically reactive conditions, to CD22. The antibody is allowed to bind to CD22 under immunologically reactive conditions, and the presence of the bound antibody is detected directly or indirectly.

Due to the increased affinity of the antibodies of the invention, the antibodies will be especially useful as diagnostic agents and in in vitro assays to detect the presence of CD22 in biological samples. For example, the antibodies taught herein can be used as the targeting moieties of immunoconjugates in immunohistochemical assays to determine whether a sample contains cells expressing CD22. Detection of CD22 in lymphocytes would indicate either that the patient has a cancer characterized by the presence of CD22-expressing cells, or that a treatment for such a cancer has not yet been successful at eradicating the cancer.

In another set of uses for the invention, immunotoxins targeted by antibodies of the invention can be used to purge targeted cells from a population of cells in a culture. Thus, for example, cells cultured from a patient having a cancer expressing CD22 can be purged of cancer cells by contacting the culture with immunotoxins which use the antibodies of the invention as a targeting moiety.

EXAMPLES

Example 1

HA22 is a recently developed, improved form of BL22, in which residues SSY in the CDR3 of the antibody variable region heavy chain (H-CDR3) were mutated to THW. HA22 is described in detail in Salvatore, G., et al., *Clin Cancer Res*, 8(4):995-1002 (2002) and in co-owned application PCT/US02/30316, International Publication WO 03/027135).

To see if the affinity of HA22 could be further improved, a phage-display library (LibVL30/31) targeting a hot spot within the light chain CDR1 (L-CDR1) of HA22 was constructed. The sequence analysis of ten clones from mutant library LibVL30/31 showed that the targeted hot spot was randomized by PCR (Table 1).

TABLE 1

Sequence analysis of mutant library LibVL30/31-3

| Clone | nt | aa |
|---|---|---|
| **Wild Type** | **AGCAAT** | **Ser-Asn** |
| 1 | CACCTG | His-Leu |
| 2 | TACCAG | Tyr-Gln |
| 3 | TTCGGC | Phe-Gly |
| 4 | GAGGCC | Gly-Ala |
| 5 | ACCTGC | Thr-Cys |
| 6 | AGGAAC | Arg-Asn |
| 7 | GAGAGC | Gly-Ser |
| 8 | TGCGTG | Cys-Val |
| 9 | TGCTGG | Cys-Trp |
| 10 | AGCATG | Ser-Met |

Subtractive Biopanning of Phage Display Libraries and FACS Analysis

In order to mimic somatic hypermutation in the immune response, high affinity against CD22+ Daudi cells and CD22− MCF7 cells.

Subtractive panning was performed on CD22 negative MCF7 cells and enrichment was performed on Daudi cells. Cells ($1\times10^7$) were pelleted and resuspended in 1 ml of cold blocking buffer. Phage ($\sim1\times10^{12}$) from the libraries were added to the cell suspension and the mixture was rotated slowly at 4° C. for 90 min. At the last step, the Daudi cells were washed 16 times with PBS/EDTA/Blocking buffer. Each wash included an incubation for 15 min on ice. Then, bound phages were eluted (pH 1.5) (Table 2). The total duration of the off-rate selection was about 4 hrs. Fluorescence activated cell sorting (FACS) analysis of the bound phage was used to monitor the enrichment of high binders after each biopanning. To our knowledge, it is the first report of the use of FACS to quantitatively monitor the enrichment of high binders in polyclonal phage antibody pool of biopanning. After the $3^{rd}$ round of biopanning, monoclonal scFvs were prepared from 32 individual clones and tested for their ability to bind to recombinant single chain CD22β-Fc by ELISA and native CD22(αβ) on Daudi cells by flow cytometry (Table 3).

TABLE 2

Enrichment of binding phage

| Library | Cycle | Input | Output | Enrichment |
|---|---|---|---|---|
| LibVL30/31 | 1 | $2\times10^{11}$ | $1.4\times10^4$ | — |
| | 2 | $2\times10^{11}$ | $7\times10^5$ | 50 |
| | 3 | $2\times10^{11}$ | $1.5\times10^8$ | 214 |

Individual phage antibodies enriched from subtractive biopanning were analyzed on Daudi cells by flow cytometry (Table 3).

TABLE 3

Monoclonal phage FACS analysis on Daudi cells and sequences of mutant phage

| Clone Name | Mean Fluorescence Intensity | Mutation sequence |
|---|---|---|
| HA22 (template) | 130 | AGC-AAG-Ser-Asn |
| B5 | 237 | CAC-GGC-His-Gly |
| B6 | 132 | TCG-GGC-Ser-Gly |
| E8 | 178 | GGG-CGG-Gly-Arg |
| H6 | 138 | CCG-TCG-Pro-Ser |
| B8 | 157 | CGC-GGG-Arg-Gly |
| D8 | 184 | GCG-CGG-Ala-Arg |

Four mutant phage antibodies (B5, E6, B8 and D8, shaded) had binding affinity for CD22-positive cells higher than the starting molecule (HA22). The order of their relative affinity (from high to low) is B5>E6~D8>B8. It is worth noting that basic amino acids (Arginine and Histidine) were dominantly selected among higher binders (shaded).

Interestingly, several mutated hot spot residues in the evolved antibodies arise from double mutations at the first and second positions (or even triple mutations) in each codon, which rarely occurs in the process of somatic hypermutation in B cells. For example, changing from AGC-AAG (Ser-Asn) in the native mouse antibody into CAC-GGC (His-Gly) in mutant B5 involves five nucleotide point mutations, in which all four nucleotides in the first and second positions are mutated. It is improbable that such dramatic mutations can occur in vivo because it is documented that hot spot mutagenesis in the somatic hypermutation process often involved only one nucleotide point mutation in each codon (also supported by the data shown Table 6). In a previous study, Salvatore et al. obtained a high binder (HA22) with mutation of ACG-CAC-TGG (Thr-His-Trp) at the AGT-AGC-TAC (Ser-Ser-Tyr) site in the H-CDR3 region using phage display technique. The only double mutation at the first and second positions resulted in the presence of Histidine. This observation strongly suggests an advantage of in vitro hot spot-based antibody evolution as compared to in vivo hot spot-based somatic hypermutation. This may also explain why some hot spot mutations favorable for higher binding affinity fail to occur in vivo.

In addition to the binding affinity, the specificity of the mutant phage was examined by measuring their binding to MCF7 cells. When tested on CD22-negative MCF7 cells, some mutants (e.g., B5) showed reduced non-specific binding as compared to HA22 (Table 4), indicating that subtractive panning can possibly enrich for mutants that have lower non-specific binding than the starting molecule.

TABLE 4

Monoclonal phage FACS analysis on MCF7 cells

| Clone Name | background binders % of total | MFI (scFv/Daudi) |
|---|---|---|
| HA22 | 9.0 | 69 |
| B5 | 3.4 | 39 |
| E6 | 4.2 | 50 |
| B8 | 4.5 | 60 |
| D8 | 4.8 | 51 |

Cytotoxic Activity (IC50)

Single chain Fv (scFv) molecules from selected phages were subcloned into a T7 expression vector in which the scFv was fused to a truncated version of *Pseudomonas* exotoxin A (PE38). After expression and purification, the recombinant immunotoxins were tested on several CD22-positive cell lines for measuring cytotoxic activity (IC50). The subtractive panning format successfully evolved several variant immunotoxins with 2-fold increases in activity (IC50) as compared with their starting molecule (HA22) (Table 5) and 8-fold increases (IC50) as compared with original BL22.

TABLE 5

Cytotoxic Activity (IC50) in ng/ml of selected RFB4 (scFv)-PE38 mutants on three different CD22-positive cell lines. Cells were incubated with immunotoxins for 16 hr and protein synthesis measured. (Note: H11 and E12 were mutants from phage library LibVH30/31 targeting H-CDR1. ND: not done).

| Mutants | CDR | Daudi | Daudi (30 min incubation) | Namalwa | Ramos |
|---|---|---|---|---|---|
| HA22 | H-CDR3 | 0.52 | 5.6 | 1.2 | 4.9 |
| B5 | L-CDR1 | 0.24 | 2.6 | 0.6 | 2.6 |
| B8 | L-CDR1 | 0.28 | N/D | 0.8 | 3.8 |
| E6 | L-CDR1 | 0.24 | 3.6 | 0.6 | 2.6 |
| D8 | L-CDR1 | 0.21 | 2.6 | 0.8 | 3.8 |
| H11 | H-CDR1 | 0.50 | N/D | 1.2 | 4.8 |
| E12 | H-CDR1 | 0.56 | N/D | 1.4 | 4.9 |

Common hot spots in CDRs may be good candidates for in vitro antibody evolution.

TABLE 6

Common and uncommon hot spots of RFB4

| CDR | Hot spot | Germline Sequence | Common | Uncommon |
|---|---|---|---|---|
| Light chain | | | | |
| CDR1 | **AGC-AA**T (Ser-Asn) | **AGC-AA**T (Ser-Asn) | ✓ | |
| CDR2 | none | | | |
| CDR3 | **GGT-A**AT-A (Gln-Gly) | GAT-**AGT-A** (Asp-Ser) | | ✓ |
| Heavy chain | | | | |
| CDR1 | **AGT-A**TC (Ser-Ile) | **AGT-AGC** (Ser-Ser) | | ✓ |
| CDR2 | **AGT-AGT** (Ser-Ser) | **AGT-AGT** (Ser-Ser) | ✓ | |
| | **GGT-A**CC (Gly-Thr) | **AGT-T**AC (Ser-Tyr) | | ✓ |
| CDR3 | N/A | | | |

Note:
Hot spots (A/G-G-C/T-A/T or A-G-C/T) are in bold. There is no hot spot in light chain CDR2 region. Comparison with germline sequence is not possible for heavy chain CDR3 region.

As shown in Table 6, the light chain CDRs and heavy chain CDR1 and 2 regions, contain five DNA hot spots. Three of them are different from their germline sequences (called for purpose of this comparison "uncommon" sequences) and two are the same as the germline sequences (herein called a sequence "common" to the two). In this study, two phage display libraries were made. One, LibVL30/31 targeted the common hot spot in L-CDR1, AGC-AAT (Ser30-Asn31), and the other, LibVH30/31, targeted H-CDR1, AGT-ATC (Ser-Ile), an uncommon hot spot. The data show that LibVL30/31 successfully produced several mutants with an affinity higher than that of the starting molecule and the immunotoxins made from them showed increased activity. But none of the selected binders enriched from LibVH30/31 (H11 and E12 in Table 5) showed significantly higher affinity and the immunotoxins made from them did not show increased cytotoxic activity.

These results may indicate that the common hot spot sequences (especially for those located in CDR1 and 2) may be good candidates for in vitro antibody evolution. CDR3 has a large somatic insertion. Previous study targeting a hot spot motif in heavy chain CDR3 of RFB4 obtained a mutant (HA22) with an affinity higher than the original antibody. This hot spot motif (AGT-AGC-TAC or Ser-Ser-Tyr) was found at the same site in many irrelevant antibodies (e.g., AY182711, AF178590 in GenBank), indicating the hot spot motif was not evolved after somatic insertion. The hypothesis is also supported by other hot spot-based in vitro antibody maturation studies (e.g., SS and evolved SS1 anti-mesothelin antibodies) previously done in our laboratory. Unlike uncommon hot spot residues, common hot spot motifs have not been mutated in vivo because of (1) possible limitation for dramatic changes or (2) low selection pressure. It is possible that some common hot spots do not directly contact with antigen, so the selection pressure is not high enough for in vivo evolution. But a more stringent selection in vitro and the potential for more dramatic changes provide a very different prospective for antibody affinity maturation.

Example 2

This Example sets forth the materials and methods in the studies reported in Example 3.

Site-Directed Mutagenesis

Mutations were introduced using two-step overlap PCR method and the RFB4 ($V_H$-GTHW (SEQ ID NO:29))—PE38 plasmid DNA used as template. Mutagenic primers that contain mutated sites (bold letter) and restriction endonuclease sites of Sal I and EcoRI (underlined) are as follows: primer A (5'-GAACCCGACGCAGCC GGCCGTATCCGCAAC-3' (SEQ ID NO:25), upstream) and primer B (5'-GTTGCGGATA CGGCCGGCTGCGTCGGGTTC-3' (SEQ ID NO:26), downstream) and primer C (5'-GCTGTCGTGGAACCAGGTCGACCAGG-3' (SEQ ID NO:27)) and primer D (5'-CTTT GTTAGCAGCC GAATTCATATTCGAT-3' (SEQ ID NO:28)).

First, PCR reactions were amplified using primers A and D or primers B and C. The PCR profiles for 1$^{st}$ reactions were as follows: 30 cycles of 1-min denaturation at 95° C., 1.3-min annealing at 58° C., and a 2-min extension at 74° C., followed by a final 5-min incubation at 72° C. A portion (0.01 ml) of each of 1$^{st}$ reactions was combined and used directly in a second PCR with only primers C and D. The PCR profile for 2$^{nd}$ reaction was as follows: 30 cycles of 1-min denaturation at 96° C., 1-min annealing at 60° C., and a 2-min extension at 72° C., followed by a final 5-min incubation at 72° C. This reaction generated a 1,000 base pair product that contained the mutation. DNA amplified using this procedure was then cloned into the Invitrogen T/A cloning vector pCR II (Invitrogen, San Diego, Calif.) without further purification, transformed into *E. coli* DH5α; and identified using blue-white screening procedures. Positive clones were sequenced using the primers C and D. The mutated insert was removed from pCR II by digesting the Plasmid with Sal I and EcoRI endonuclase and the fragment was ligated to identical digested VH-PE38 plasmid.

Expression and Purification of HA22 (R490A)

The immunotoxins used in the studies herein were made as disulfide-stabilized Fvs. The two chains are engineered with cysteines to permit disulfide bonding, expressed separately in *E. coli* and allowed to bond before purification from the inclusion bodies (in these studies, the heavy chain was expressed as a fusion protein with the toxin moiety). In particular, the immunotoxins were expressed in *E. coli* BL21 (λDE3) and accumulated in inclusion bodies, as previously described for other immunotoxins (Reiter, Y., et al., *Biochemistry,* 33(18):5451-9 (1994)). Inclusion bodies were treated with lysozyme and washed by homogenization and centrifugation with 2.5% Triton X-100 and 0.5M NaCl, 4×, followed by rinsing and homogenization and centrifugation in TE buffer without Triton X-100 and NaCl 4×. The inclusion body protein was dissolved, denatured and reduced in guanidine-dithioerythritol solution. Reducing solutions, containing 67 mg of RFB4 ($V_H$-GTHW (SEQ ID NO:29))-PE38 (R490A) or 33 mg of RFB4 ($V_L$), each at a protein concentration of 10 mg/ml, were combined and then renatured by 100-fold dilution into a redox buffer containing L-arginine and oxidized glutathione (Mansfield, E., et al., *Blood,* 90(5):2020-6 (1997)). The protein was refolded at 10° C. for 40 hr. The refolded protein was dialyzed with 20 mM Tris, pH 7.4, containing 0.1 M urea and the precipitated aggregates removed by centrifugation. The protein was then applied to 10 ml of Q-Sepharose (Pharmacia, Piscataway, N.J.), which was washed with 20 mM Tris, pH 7.4, and eluted with 20 mM Tris, pH 7.4, containing 0.3 M NaCl. The Q-Sepharose-purified protein was then diluted 5-fold with 20 mM Tris, pH 7.4, and loaded onto a 10 ml Mono-Q (Pharmacia) column, which was eluted with a linear gradient to obtain protein. The concentrated Mono-Q purified protein was then loaded on a Superose-12 (Pharmacia) column and 6 mg of protein (6% of total recombinant protein) was obtained by elution with PBS. The final endotoxin content was 0.86 EU/mg protein. Protein concentrations were determined by Bradford Assay (Coomassie Plus; Pierce, Rockford, Ill.).

Cytotoxicity Assay. The specific cytotoxicity of HA22 (R490A) was determined by protein synthesis inhibition assays (inhibition of incorporation of tritium-labeled leucine into cellular protein) in 96-well plates. Cells were maintained in RPMI 1640 containing 10% fetal bovine serum (FBS), 50 μg/ml penicillin, 50 μg/ml streptomycin, 1 mM sodium pyruvate, and 2 mM L-glutamine. For cytotoxicity assay, $1.5\times10^4$ cells in 200 μl of culture medium were plated in 96-well plates. For cytotoxicity experiements with Daudi, CA46, Raji, JD38 and A431 cells, immunotoxins were serially diluted in PBS/0.2% BSA and 20 μl was added to cells. Plates were incubated for 20 hr at 37° C. and then pulsed with 1 μCi/well [$^3$H]-Leucine in 20 μl of PBS/0.2% BSA for 4 hr at 37° C. Triplicate sample values were averaged, and inhibition of protein synthesis was determined by calculating percent incorporation compared to control wells without added toxin. The concentrations of immunotoxin that reduced [$^3$H]-Leucine incorporation by 50% relative to untreated control culture were defined as the $IC_{50}$.

Cell Viability Assay. Inhibition of cell growth upon treatment with HA22 (R490A) was determined in standard WST assays based on the reduction of tetrazolium salt to formazan by the enzymes from viable cells. Absorbance was measured in an enzyme-linked immunosorbent assay (ELISA) reader at 450 nm, with the absorbance at 650 nm to correct for background, and viability was expressed as percentage of untreated controls.

CA46 cells were plated at 8,000/well in a 96-well plate. HUVECs human umbilical vein endothelial cells) were grown in endothelial cell growth medium (EGM) plus bovine brain extract, both purchased from Clonetics Corp. (San Diego, Calif.). Cells were seeded in 96-well plates at 3,000 cells/well. Immunotoxins were serially diluted in culture media and 10 μl was added to cells. Plates were incubated for 40 hr or for 72 hr (HUVEC) at 37° C. Then 5 μl of WST-8 (2-(2-methoxy-4-nitrophenyl)-3-(4-nitrophenyl)-5-(2,4-disulfophenyl)-2H-tetrazolium, monosodium salt) solution was added to each well of the plate and the cells were incubated for 4 hr at 37° C. The optical density at 450 and 650 nm was determined using an ELISA reader. Triplicate sample values were averaged, and viability was determined by calculating percent viability compared to control wells without added toxin. To correct for background activity, cells were cultured in the presence of cycloheximide (Sigma) at 10 μg/mL. This was calculated using the following equation: (Absorbance of cells without immunotoxin Absorbance of cells cultured with cycloheximide)/(Absorbance of cells cultured in the presence of immunotoxin/Absorbance of cells cultured with cycloheximide).

Preparation of SS1P (R490A)

A mutant at 490 (R490A) was constructed by PCR-based sited directed mutagenesis. DNA amplified using this procedure was then cloned into the Invitrogen T/A cloning vector pCR II without further purification, transformed into *E. coli* DH5α, and identified using blue-white screening procedures. The mutated insert was removed from pCR II by digesting the plasmid with Sal I and EcoRI endonuclase and the fragment was ligated to identical digested $SSV_H$-PE38 plasmid.

The immunotoxins used in the studies herein are dsFvs, in which the two chains are expressed separately in *E. coli* and allowed to bond before purification from the inclusion bodies (in these studies, the heavy chain was expressed as a fusion protein with the toxin moiety). The immunotoxins were expressed in *E. coli* BL21 (λDE3) and accumulated in inclusion bodies, which expressed either $SSV_H$-PE38 (R490A) or SS1 ($V_L$) as previously described for other immunotoxins (Reiter, Y., et al., *Biochemistry,* 33(18):5451-9 (1994)).

Cytotoxicity Assay. The specific cytotoxicity of SS1P (R490A) and SS1P were evaluated on two mesothelin-positive cancer cell lines A431/K5, an epidermoid carcinoma cell line transfected with full-length mesothelin cDNA, and A1847 using a protein synthesis inhibition assay. Cells ($1.5\times10^4$) in 200 μl of culture medium were plated in 96-well plates. After 24 hr immunotoxins were serially in PBS/0.2% BSA and 20 μl was added to cells. Plates were incubated for 20 hr at 37° C. and then pulsed with 1 μCi/well [$^3$H]-Leucine in 20 μl of PBS/0.2% BSA for 2 hr at 37° C. Triplicate sample values were averaged, and inhibition of protein synthesis was determined by calculating percent incorporation compared to control wells without added toxin. Concentrations of immunotoxin that reduced [$^3$H]-Leucine incorporation by 50% relative to untreated control culture were defined as the $IC_{50}$.

Cell Viability Assay. A431/K5 or A1847 cells were plated at 8,000/well in 96-well plate. After 24 hr immunotoxins were serially diluted in culture media and 10 μl was added to cells. Plates were incubated for 40 hr at 37° C. Add 10 μl of WST-8 (2-(2-methoxy-4-nitrophenyl)-3-(4-nitrophenyl)-5-(2,4-disulfophenyl)-2H-tetrazolium, monosodium salt) solution was added to 100 μl medium per well and incubate for 1 hr at 37° C. The optical density at 450 and 650 nm was determined using an ELISA reader. Triplicate sample values were averaged, and viability was determined by calculating percent viability compared to control wells without added toxin.

Nonspecific Toxicity Assay. On day 0, female Swiss mice (5~6 wks, 18~22 g weight) were given a single injection into the tail vein of various amounts of immunotoxin in 0.2 ml of PBS containing 0.2% HSA. Animal mortality was observed over 2 wk.

Pharmacokinetics

NIH Swiss mice were injected into the tail vein with 10 μg of BL22, or HA22, or HA22 (R490A). Blood samples were drawn at different times from the tail vein. The concentration of IT in the circulation was determined by an ELISA method. Purified immunotoxin was used to construct a standard curve.

ELISAs

Immunotoxin levels in serum were measured using the following ELISA. Microtiter plates were coated with 50 μl of CD22-Fc protein (5 μg/ml) in PBS at 4° C. overnight. The plates were blocked within PBS buffer containing 3% BSA at room temperature for 2 hr, followed by five times washes in PBST (PBS containing 0.05% Tween-20). Standards and samples were diluted 1/100, 1/500, and 1/1000 in phosphate-buffered saline (PBS) with 1% normal mouse serum. 100 μl of diluted standards or samples were added and incubated in the coated ELISA plates at 4° C. overnight. The plates were washed five times in PBST, followed by incubation with 50 μl of 1:250 dilution of HRP-conjugated anti-PE antibody for 3 hr at room temperature. After washing five times in PBST, the color was developed with TMB for 10 min and the optical density (OD) was read at 450 and 650 nm. The assays conducted during the development phase were performed in triplicate.

Anti-tumor Activity

The anti-tumor activity of the ITs was determined in SCID mice bearing CA46 cells. Cells ($1\times10^7$) were injected s.c. into SCID mice (4~5 wks, body weight 16~18 g) on day 0. Tumors ~100 $mm^3$ in size developed in animals by day 6 after tumor implantation. Starting on day 6, animals were treated with i.v. injections of each of the ITs diluted in 0.2 ml of PBS/0.2% HSA. Therapy was given once every other day (QOD×3; on days 6, 8, and 10), and each treatment group consisted of eight or ten animals. Tumors were measured with a caliper every 2 or 3 days, and the volume of the tumor was calculated by using the formula: tumor volume ($cm^3$)=length×(width)$^2$×0.4.

Statistics

For statistical analysis between two groups of data, the two-tailed Student's t test was performed. P values<0.05 were considered to be significant.

Example 3

This Example sets out the results of experiments conducted with R490A mutated PEs.

HA22 is a recombinant immunotoxin that has a high affinity for CD22 and is very active in killing cells from B cell malignancies that express CD22. The goal of the present study was to make a mutant of HA22 resistant to proteolytic digestion and, hopefully, therefore increased anti-tumor activity, either because of less non-specific intracellular proteolytic degradation or decreased degradation in the circulation. Previous studies had shown that destruction of a proteolytic digestion site brought about by deletion of arginine 490 in domain 3 of native PE resulted in an increase in the half-life of PE in the circulation of mice. To minimize any changes in protein structure that a mutation at position 490 might introduce, R490 was mutated to alanine rather than deleted, as was done previously with native PE (Brinkmann, U., et al., *Proc Natl Acad Sci USA,* 89(7):3065-9 (1992)).

Preparation and Characterization of Immunotoxins. Immunotoxins HA22 and HA22 (R490A) and other immunotoxins were constructed and purified as described in the previous Example. For purposes of the present studies, all of the immunotoxins made were disulfide-linked immunotoxins in which the $V_L$ is attached to VH-PE38 by a disulfide bond. To make these proteins each of the two components is expressed separately in *E. coli* and recombined before renaturation. The renatured disulfide-linked immunotoxin is then purified by ion exchange (Q-Sepharose, Mono-Q) and gel filtration column chromatography (Superose-12). The final yield of the purified HA22 (R490A) protein is 6% of the starting inclusion body protein and that of HA22 is 8%. FIG. 4A shows the elution profile of HA22 (R490A) from a Suberose-12 gel filtration column. The chromatogram shows the presence of one peak eluting in fractions 11 to 15 that is the position expected of a protein with a molecular weight of 63 kDa. No high molecular weight aggregates were detected. FIG. 4B shows the SDS-PAGE analysis of the peak fraction (fraction 12). HA22 (R490A) migrates as single band with the expected molecular weight of 63 kDa in a non-reducing gel. Under reducing conditions, the single band is resolved into two bands, which correspond to $V_L$ and $V_H$-PE38. This indicates the dsFv immunotoxin is properly folded into a monomer. The other immunotoxins were prepared in a similar manner as previously described (Kreitman, R. J., et al., *Int J Cancer,* 81(1):148-55 (1999)) and their purity was comparable to HA22 (R490A).

Figure 5:
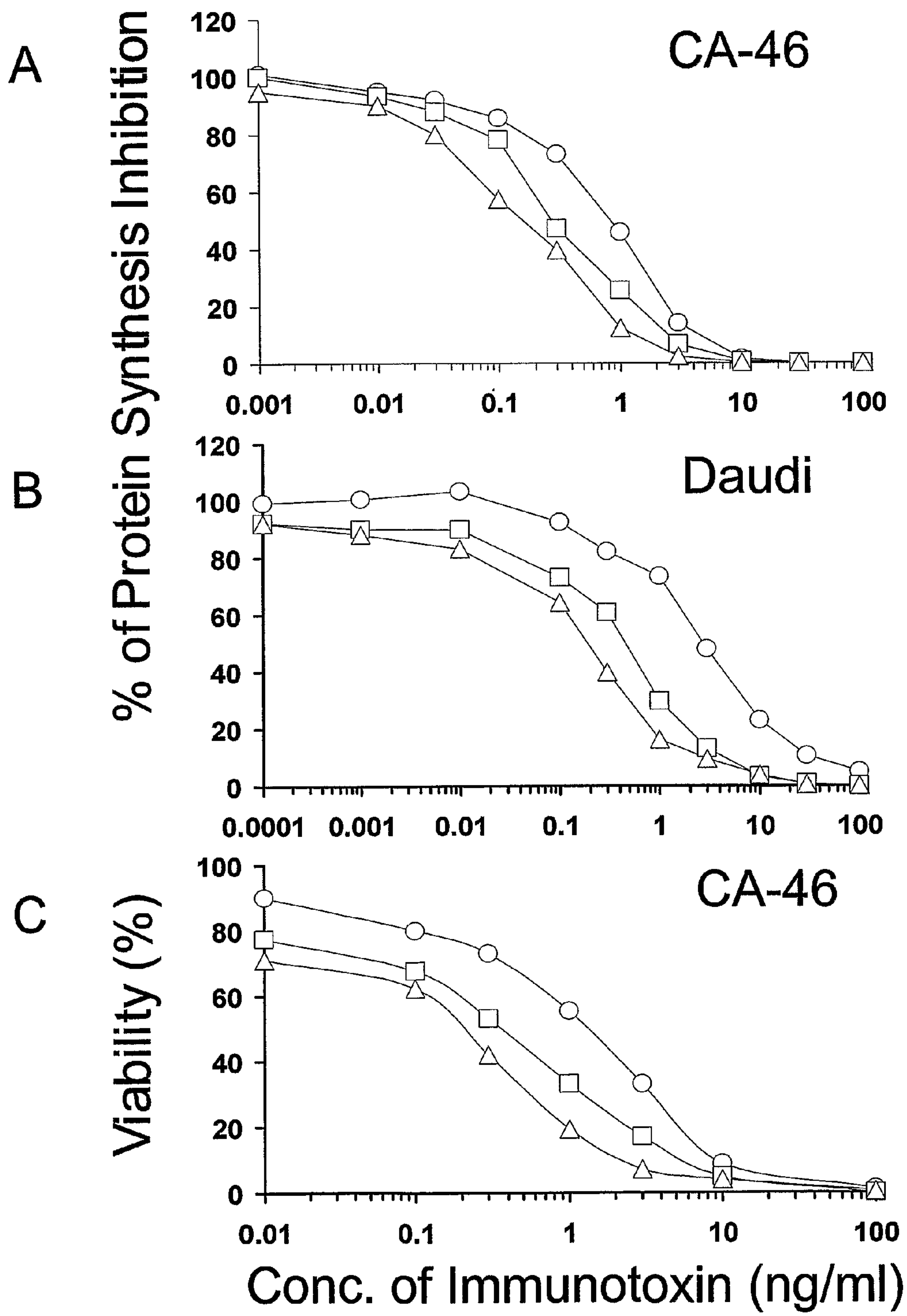
FIGS. 5A-C.

Cytotoxicity of HA22 (R490A). The cytotoxic activities of HA22, HA22 (R490A) and BL22 were evaluated on several CD22 positive B cell lymphoma cell lines (Daudi, CA46, and Raji) and on one CD22 negative epithelial cancer cell line (A431) using a protein synthesis inhibition assay. These values were compared with the activity of BL22, the immunotoxin from which HA22 was derived (Table 7). As shown in FIG. 5 and summarized in Table 7, HA22 (R490A) is 2-fold more active on Daudi and on CA46 cells as compared with HA22 and is 3-fold more active on Raji cells. BL22 is much less active than either immunotoxin on these cell lines. The immunotoxins were also tested on the CD22 negative A431 cell line and found to be about 1000-fold less toxic, demonstrating that these immunotoxins are quite specific for CD22 expressing cells.

Cell Viability Assay. The activities of the immunotoxins were also assessed on CA46 cells using a cell viability assay with WST-8 as a specific substrate (Bai, et al., *Free Radic. Biol. Med* 30:555-562 (2001). The results are expressed as the percentage of untreated control cells (FIG. 5C). The concentrations of HA22 (R490A), HA22 or BL22 required to cause 50% inhibition ($IC_{50}$) of cell viability are 0.18 ng/ml 0.32 ng/ml and 1.3 ng/ml, respectively. The magnitude of the differences in activities among these three immunotoxins shows the same dose-response relationship as for the inhibition of protein synthesis assays described above.

Figure 6:
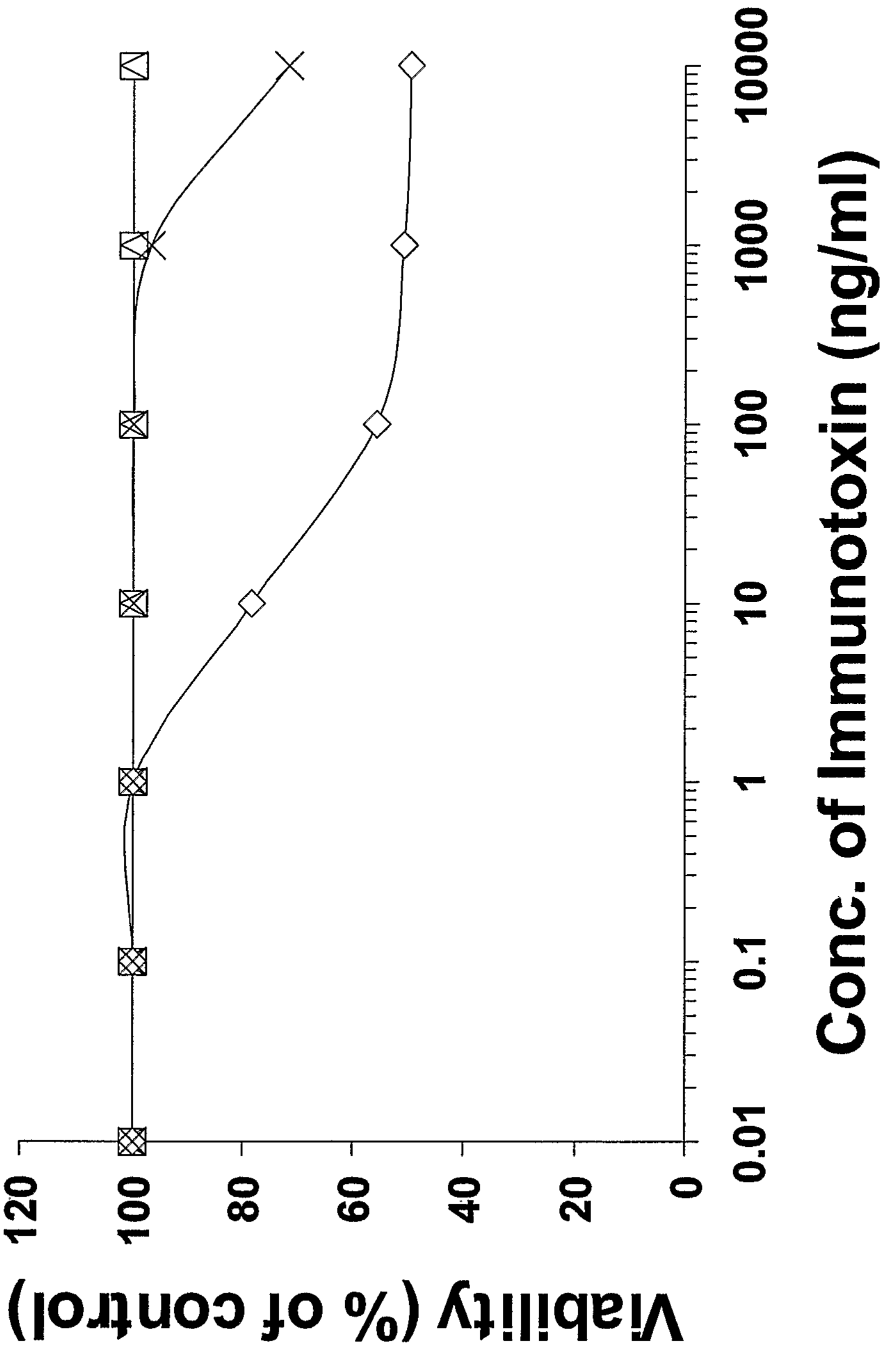
FIG. 6. Cell viability assay of HUVEC cells contacted with various immunotoxins. HUVEC ($3\times10^3$ cells/well) were incubated with various concentrations of immunotoxins for 72 hr. Cell viability was determined by WST conversion assay as described in Example 2. The assays show that immunotoxins directed to other cell receptors are more toxic to HUVEC cells than are BL22, HA22, and HA22(R490A). Results are given as % viability without immunotoxin incubation and represent the mean of triplicate values. Legend: ○, BL22; □, HA22; Δ, HA22 (R490A); ◇, HB21Fv-PE40; and X, LMB-7.

To further assess specificity, whether HA22 (R490A) could result in induction of endothelial cell death was examined. Endothelial cells were chosen because endothelial cells do not express CD22, but may have a role in the toxic side effects of some immunotoxins (Vitetta, E. S., *Cancer J,* 6 Suppl 3:S218-24 (2000)). The endothelial cell line HUVEC (human umbilical vein endothelial cells, commercially available from, for example, Cambrex BioScience Baltimore Inc., Baltimore, Md.) was treated with either HA22 (R490A), HA22, BL22, HB21(Fv)-PE40 or LMB-7. HB21(Fv)-PE40 targets the transferrin receptor that is widely expressed on many cell types and was expected to be cytotoxic to HUVEC cells. LMB7 targets the $Le^Y$ antigen previously shown to be expressed on HUVEC cells (Mansfield, E., et al., *Bioconjug Chem,* 7(5):557-63 (1996)). As shown in FIG. 6, neither HA22 (R490A), HA22 or BL22 decreased the viability of HUVECs. However, as expected both HB21(Fv)-PE40 and LMB7 were cytotoxic to the cells. These results further confirm the specificity of HA22 (R490A).

Mouse Studies. Because HA22 (R490A) was more cytotoxic to the CD22-positive cell lines than HA22, its antitumor activity was compared with that of HA22. Before doing this, its LD50 to mice was determined to ensure the new immunotoxin did not have high toxicity to mice. Groups of mice consisting of 5 or more members were given a single i.v. injection of various doses of HA22 (R490A), HA22 or BL22 and observed for 2 wk. Table 8 shows the toxicity data. HA22 and HA22 (R490A) have very similar animal toxicities with $LD_{50}$s of about 1.3 mg/kg. BL22 was slightly more toxic with all mice dying at a dose of 1.25 mg/kg. Almost all of the deaths occurred within 72 hr after treatment. These data show that the R490A mutation has very little effect on mouse toxicity.

Figure 7:
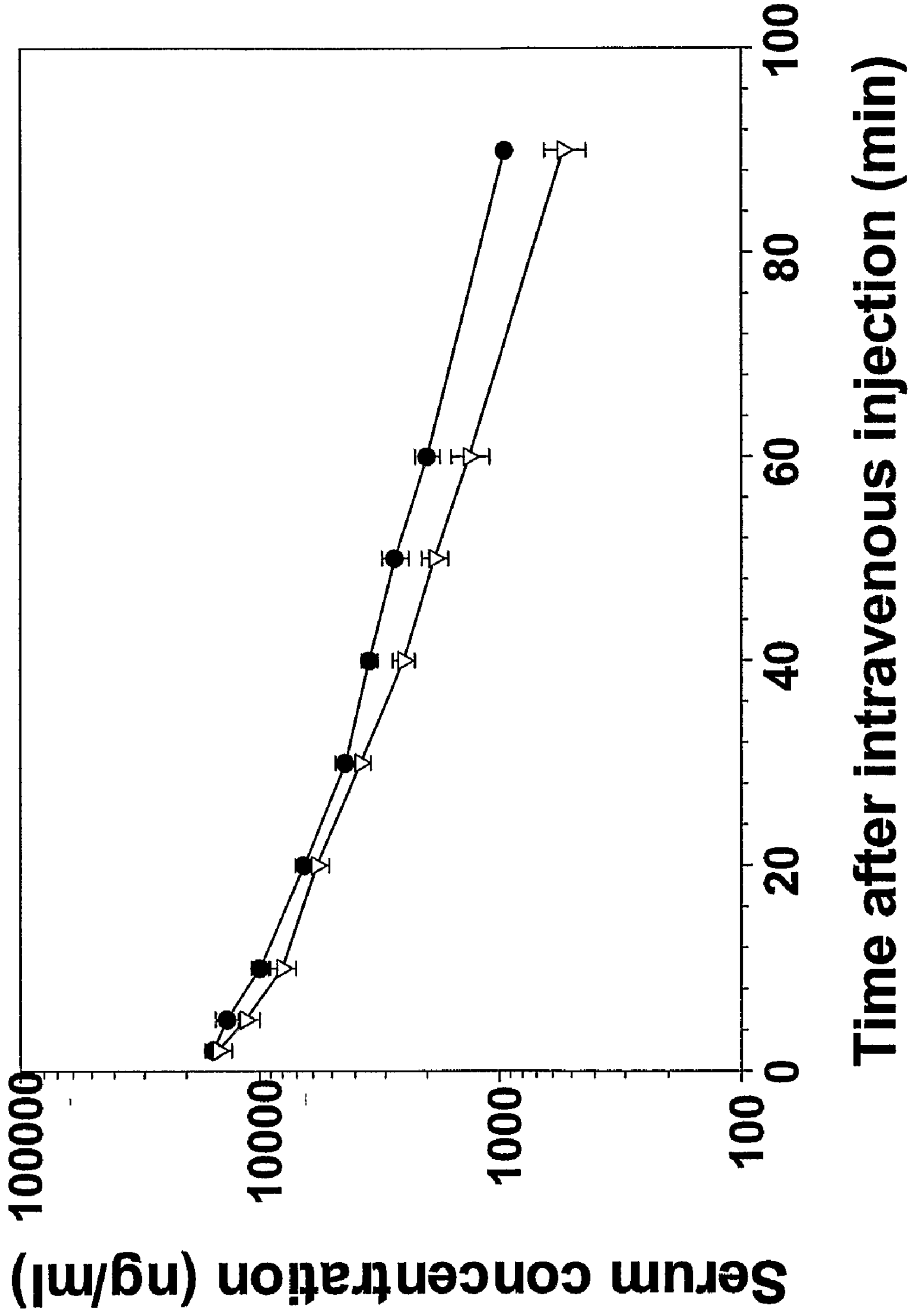
FIG. 7. Pharmacokinetics of HA22 (R490A) in mice. Normal female Swiss mice were injected i.v. with 10 μg of HA22 (●) or HA22 (R490A) (∇). Blood samples were drawn at times shown. The concentration of each immunotoxin in the circulation was determined by ELISA.

Pharmacokinetics. Another important parameter of antitumor activity is the length of time the immunotoxin remains in the circulation and is able to interact with the tumor cells. To determine the $t_{1/2}$ of HA22 (R490A) and other immunotoxins in the mouse circulation, mice were injected i.v. with a single dose of 10 μg of BL22, HA22 or HA22 (R490A). Blood samples were drawn from the tail vein at different times after the injection of each agent and the levels of each of the immunotoxins in the plasma were measured by an ELISA. FIG. 7 shows the plasma concentration profiles of HA22 and HA22 (R490A) over a 90 min period. Each data point is the average of samples from four animals. The plasma half-life of HA22 is 21.9 min, compared to a half-life of 18.8 min for HA22 (R490A) (Table 9). The half-life of BL22 is longer, 27.7 min. Thus the R490A mutation reduces half-life by a small amount.

TABLE 7

Cytotoxicity activity (IC50) in ng/ml of BL22 and mutant ITs toward various cell lines

| | CD22-positive cell lines (Burkitt lymphoma) | | | CD-22 negative cell line (Epidermoid) |
|---|---|---|---|---|
| | Daudi | CA46 | Raji | A431 |
| BL22 | 2.8 | 0.82 | 2.5 | >1,000 |
| HA22 | 0.45 | 0.28 | 0.9 | 500 |
| HA22 (R490A) | 0.2 | 0.15 | 0.3 | 300 |

Cytotoxicity data are given as $IC_{50}$s, which are the concentrations of immunotoxin that cause a 50% inhibition in protein synthesis compared with controls after incubation with cells for 24 hr.

TABLE 8

Non-specific toxicity in mice of HA22 and HA22 (R490A)

| IT | Dose (mg/kg) | Death/Total |
|---|---|---|
| BL22 | 0.75 | 0/10 |
| | 1.0 | 1/14 |
| | 1.25 | 14/14 |
| | 1.5 | 9/9 |
| HA22 | 0.75 | 0/5 |
| | 1.0 | 0/10 |

TABLE 8-continued

| Non-specific toxicity in mice of HA22 and HA22 (R490A) | | |
|---|---|---|
| IT | Dose (mg/kg) | Death/Total |
| | 1.25 | 4/10 |
| | 1.5 | 7/10 |
| | 1.75 | 9/10 |
| HA22 (R490A) | 1.0 | 0/15 |
| | 1.25 | 5/15 |
| | 1.5 | 10/15 |
| | 1.75 | 15/15 |

On day 0, female Swiss mice (5~6 wk, 18~22 g weight) were treated by tail vein single injection with various amounts of immunotoxins in 0.2 ml of PBS containing 0.2% HSA. Animal mortality was observed over 2 wk.

TABLE 9

| Pharmacokinetics in mice of immunotoxin | | | |
|---|---|---|---|
| Immunotoxin | 2 min blood level (ng/ml) | Half-life (min) | AUC* (μg/min/ml) |
| BL22 | 15,934 | 27.7 | 582 |
| HA22 | 15,502 | 21.9 | 438 |
| HA22 (R490A) | 14,857 | 18.8 | 345 |

*Area under the curve

Example 4

This Example sets out the results of experiments investigating the effect of R490A mutated PEs on animals bearing xenografts of human tumors.

Figure 8:
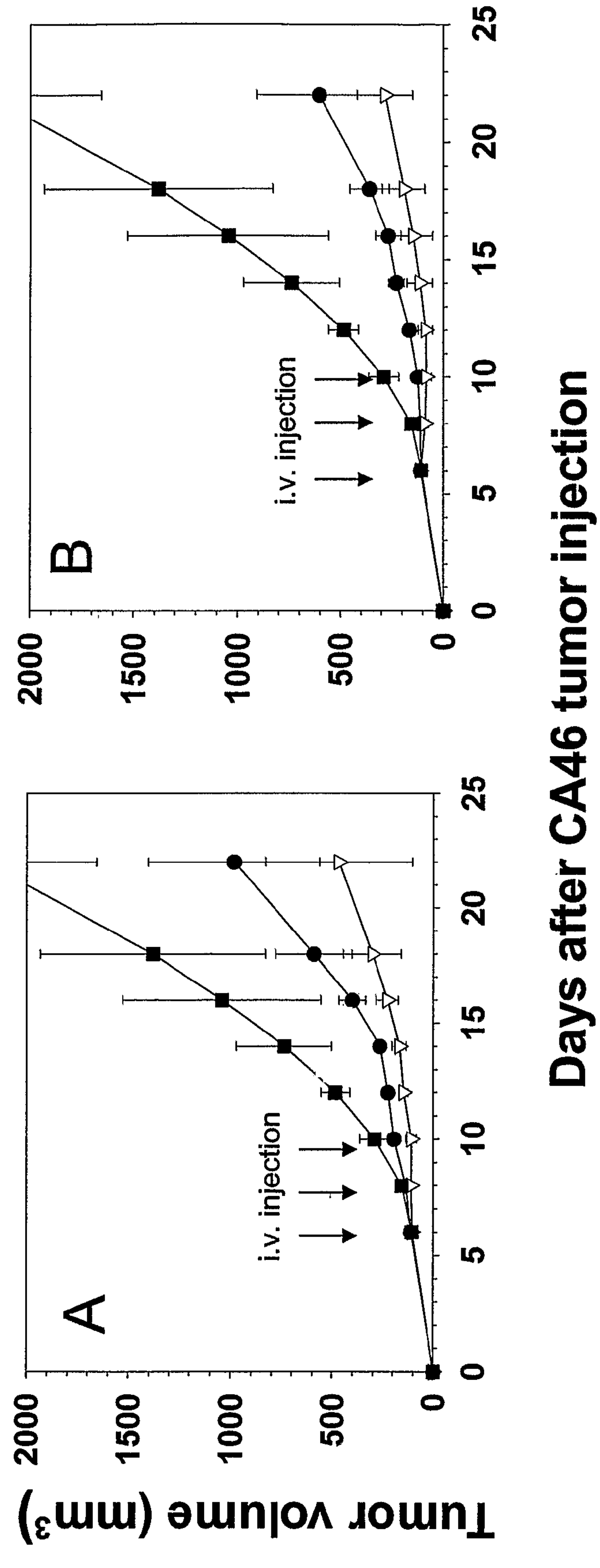
FIGS. 8A and B. Anti-tumor activities of HA22 and HA22 (R490A). Both Figures: CA46 cells were inoculated s.c. in SCID mice on day 0.
FIG. 8B: The anti-tumor response of mice treated with HA22 (●) at 300 μg/kg QOD×3 was contrasted with that of mice which were untreated (□) or treated with HA22 (R490A) 300 μg/kg QOD×3 (∇). Therapy was given once every other day (on days 6, 8, and 10; as indicated by the arrows). No death was observed at these doses. Both Figures: Error bars indicate standard deviations from the means of each group of mice. The comparisons between HA22 and HA22 (R490A) at each dose were statistically significant (P=0.01-0.001).

Anti-tumor Activity. To determine whether the improved in vitro cytotoxic activity was translated to increased anti-tumor activity, HA22 (R490A) and HA22 were compared using tumor xenografts of CA46 cells growing in SCID mice. CA46 cells ($1\times10^7$) were implanted into the flanks of SCID mice on day 0. On day 6, when the tumors reached ~100 $mm^3$ in size, the animals were injected i.v. with either 300 μg/kg (n=10) or 150 μg/kg (n=8) of HA22 or HA22 (R490A) every other day×3. As shown in FIG. 8, treatment with HA22 (R490A) or HA22 decreased tumor size compared with controls. By day 10, tumors in mice receiving 300 μg/kg of HA22 (R490A) fell to 85 $mm^3$ in size, whereas in mice treated with 300 μg/kg of HA22 the tumors were 126 $mm^3$ in size. Treatment with 150 μg/kg of HA22 (R490A) resulted in tumors averaging 358 $mm^3$ on day 18 whereas tumors treated with HA22 were significantly larger averaging 592 $mm^3$ (FIG. 8A). Anti-tumor activity was also dependent on dose; 150 μg/kg was less effective than 300 μg/kg for both immunotoxins. Without treatment, CA46 tumors grew rapidly and reached to a size of over 2,000 $mm^3$ by day 22, when the mice were sacrificed. A significant difference in tumor size (P<0.001, Student's t test) was found between the mice that received HA22 and mice that received HA22 (R490A) at 150 μg/kg on treatment day 10 (p=0.0006) on day 16 (p=0.0003); and with 300 μg/kg treatment on day 14 (p=0.00068) and day 18 (p=0.00096).

Table 10 shows the animal toxicity at each of these dose levels. There were no deaths but some weight loss. At 300 μg/kg, 2 of 10 mice treated with HA22 (R490A) and 3/10 mice treated with HA22 experienced mild weight loss (less than 5%) during the 4 days after the first injection. The mice began to regain weight 2 to 4 days after the last injection and returned to initial body weight by day 14. No significant difference in body weights was seen between the HA22 (R490A) treated group and the HA22 group. In contrast, at the 150 μg/kg dose the weight curves of the immunotoxin treated groups paralleled very closely that of the control (untreated) group. Thus, the anti-tumor effects were not due to the poor health of the animals. The data show that HA22 (R490A) has a more potent anti-tumor activity than HA22.

TABLE 10

| Toxicity of HA22 and HA22 (R490A) administered to SCID mice | | | |
|---|---|---|---|
| IT | Dose | Total dose (μg/kg) | Mortality |
| HA22 | 150 μg/kg QOD ×3 | 450 | 0/8 |
| | 300 μg/kg QOD ×3 | 900 | 0/10 |
| HA22 (R490A) | 150 μg/kg QOD ×3 | 450 | 0/8 |
| | 300 μg/kg QOD ×3 | 900 | 0/10 |

Example 5

This Example sets out the results of experiments conducted a second immunotoxin in which the PE contains the R490A mutation.

Immmunotoxin SS1P. Mesothelin is an antigen that is highly expressed on pancreatic and ovarian cancers and mesotheliomas. SS1P is a PE-based immunotoxin that binds to mesothelin and kills mesothelin expressing cells. To determine if the R490A mutation would also increase the cytotoxic activity of an immunotoxin target in an epithelial cancer, the R490A mutation was introduced into SS1P to produce SS1P (R490A). Both immunotoxins were prepared and tested on two mesothelin expressing cell lines. The data in Table 11 shows that SS1P (490A) was significantly more active than SS1P on 2 mesothelin expressing cell lines, with about a 2-fold increase in activity.

TABLE 11

| Cytotoxicity of SS1P and SS1P (R490A) | | |
|---|---|---|
| | $IC_{50}$ (ng/ml) | |
| IT | A431/K5 | A1847 |
| SS1P | 0.7 (0.75)* | 4.0 (5.1)* |
| SS1P(R490A) | 0.45 (0.43)* | 1.5 (2.3)* |

Cytotoxicity assays were performed by measuring incorporation of [$^3$H]-Leucine in cells after 20 hrs treatment with indicated concentrations of immunotoxins. $IC_{50}$ is the concentration that causes 50% inhibition of protein synthesis.
*Represents 50% cell viability. The cell viability was measured by WST-8 method. The results are expressed as a percentage of the control values in the absence of immunotoxins.

While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited herein are incorporated by reference in their entirety for all purposes to the same extent as if each individual publication or patent document were so individually denoted. Citation of various references in this document is not an admission that any particular reference is considered to be "prior art" to the invention.

What is claimed is:

1. An antibody that specifically binds CD22, said anti-CD22 antibody having a variable light (VL) chain comprising three complementarity determining regions (CDRs), and a variable heavy (VH) chain comprising three CDRs, wherein (i) said VL chain CDR1 has the sequence of SEQ ID NO:7, wherein positions 4-5 of SEQ ID NO:7 have an amino acid sequence selected from the group consisting of HG, GR, RG and AR, (ii) said VL CDR2 has the sequence of SEQ ID NO:11, (iii) said VL CDR3 has the sequence of SEQ ID NO:12, (iv) said VH CDR1 has the sequence of SEQ ID NO:13, (v) said VH CDR2 has the sequence of SEQ ID NO:14, and (vi) said VH CDR3 has the sequence of SEQ ID NO:16, wherein positions 8-10 of SEQ ID NO:16 have an amino acid sequence selected from the group consisting of THW, YNW, TTW and STY.

2. An anti-CD22 antibody of claim 1, wherein said VL CDR1 has the sequence of SEQ ID NO:7.

3. An anti-CD22 antibody of claim 1, wherein said VH CDR3 has the sequence of SEQ ID NO:16.

4. An anti-CD22 antibody of claim 1, wherein said VL chain has the sequence of SEQ ID NO:20.

5. An anti-CD22 antibody of claim 1, further wherein said VL CDR1 has the sequence of SEQ ID NO:7 and said VH CDR3 has the sequence of SEQ ID NO:16.

6. An anti-CD22 antibody of claim 1, wherein said VH chain has the sequence of SEQ ID NO:21.

7. An anti-CD22 antibody of claim 1, wherein said VL chain has the sequence of SEQ ID NO:20 and said VH chain has the sequence of SEQ ID NO:21, except that, optionally, said VL chain has a cysteine in place of glycine at position 100 and said VH chain has a cysteine in place of arginine at position 44, as these positions are numbered according to the "Kabat Numbering".

8. An anti-CD22 antibody of claim 1, wherein said antibody is selected from the group consisting of an scFv, a dsFv, a Fab, or a $F(ab')_2$.

9. A chimeric molecule comprising a therapeutic moiety or detectable label conjugated or fused to an antibody that specifically binds CD22, said anti-CD22 antibody having a variable light (VL) chain comprising three complementarity determining regions (CDRs), and a variable heavy (VH) chain comprising three CDRs, wherein (i) said VL chain CDR1 has the sequence of SEQ ID NO:7, wherein positions 4-5 of SEQ ID NO:7 have an amino acid sequence selected from the group consisting of HG, GR, RG and AR, (ii) said VL CDR2 has the sequence of SEQ ID NO:11, (iii) said VL CDR3 has the sequence of SEQ ID NO:12, (iv) said VH CDR1 has the sequence of SEQ ID NO:13, (v) said VH CDR2 has the sequence of SEQ ID NO:14, and (vi) said VH CDR3 has the sequence of SEQ ID NO:16, wherein positions 8-10 of SEQ ID NO:16 have an amino acid sequence selected from the group consisting of THW, YNW, TTW and STY.

10. A chimeric molecule of claim 9, wherein said VL CDR1 has the sequence of SEQ ID NO:7.

11. A chimeric molecule of claim 9, wherein said VH CDR3 has the sequence of SEQ ID NO:16.

12. A chimeric molecule of claim 9, wherein said VL chain has the sequence of SEQ ID NO:20.

13. A chimeric molecule of claim 9, further wherein said VL CDR1 has the sequence of SEQ ID NO:7 and said VH CDR3 has the sequence of SEQ ID NO:16.

14. A chimeric molecule of claim 9, wherein said VH chain has the sequence of SEQ ID NO:21.

15. A chimeric molecule of claim 9, wherein said VL chain has the sequence of SEQ ID NO:20 and said VH chain has the sequence of SEQ ID NO:21, except that, optionally, said VL chain has a cysteine in place of glycine at position 100 and said VH chain has a cysteine in place of arginine at position 44, as these positions are numbered according to the "Kabat Numbering".

16. A chimeric molecule of claim 9, wherein said antibody is selected from the group consisting of an scFv, a dsFv, a Fab, or a $F(ab')_2$.

17. A chimeric molecule of claim 9, wherein the therapeutic moiety is selected from the group consisting of a cytotoxin, a drug, a radioisotope, or a liposome loaded with a drug or a cytotoxin.

18. A chimeric molecule of claim 17, wherein the therapeutic moiety is a cytotoxin selected from the group consisting of ricin A, abrin, ribotoxin, ribonuclease, saporin, calicheamycin, a mutated diphtheria toxin, a mutated *Pseudomonas* exotoxin A ("PE"), and botulinum toxins A through F.

19. A chimeric molecule of claim 18, wherein said mutated PE has the amino acid sequence of SEQ ID NO:22.

20. A chimeric molecule of claim 18, wherein said mutated PE has the amino acid sequence of SEQ ID NO:23.

21. A composition comprising (a) a pharmaceutically acceptable carrier and (b) a chimeric molecule comprising an antibody conjugated or fused to a therapeutic moiety or a detectable label, wherein said antibody specifically binds CD22, said anti-CD22 antibody has a variable light (VL) chain comprising three complementarity determining regions (CDRs), and a variable heavy (VH) chain comprising three CDRs, further wherein (i) said VL chain CDR1 has the sequence of SEQ ID NO:7, wherein positions 4-5 of SEQ ID NO:7 have an amino acid sequence selected from the group consisting of HG, GR, RG and AR, (ii) said VL CDR2 has the sequence of SEQ ID NO:11, (iii) said VL CDR3 has the sequence of SEQ ID NO:12, (iv) said VH CDR1 has the sequence of SEQ ID NO:13, (v) said VH CDR2 has the sequence of SEQ ID NO:14, and (vi) said VH CDR3 has the sequence of SEQ ID NO:16, wherein positions 8-10 of SEQ ID NO:16 have an amino acid sequence selected from the group consisting of THW, YNW, TTW and STY.

22. A composition of claim 21, wherein said VL CDR1 has the sequence of SEQ ID NO:7 and said VH CDR3 has the sequence of SEQ ID NO:16.

23. A composition of claim 21, wherein the therapeutic moiety is selected from the group consisting of a cytotoxin, a drug, a radioisotope, or a liposome loaded with a drug or a cytotoxin.

24. A composition of claim 21, wherein the therapeutic moiety is a cytotoxin selected from the group consisting of ricin A, abrin, ribotoxin, ribonuclease, saporin, calicheamycin, diphtheria toxin or a cytotoxic subunit or mutant thereof, a mutated *Pseudomonas* exotoxin A ("PE"), and botulinum toxins A through F.

25. A composition of claim 24, wherein said mutated PE has the amino acid sequence of SEQ ID NO:22.

26. A composition of claim 24, wherein said mutate PE has the amino acid sequence of SEQ ID NO:23.

27. A method of inhibiting growth of a CD22+ cancer cell, wherein said method comprises contacting said cell with a chimeric molecule comprising (a) an antibody that binds to CD22, said anti-CD22 antibody has a variable light (VL) chain comprising three complementarity determining regions (CDRs), and a variable heavy (VH) chain comprising three CDRs, further wherein (i) said VL chain CDR1 has the sequence of SEQ ID NO:7, wherein positions 4-5 of SEQ ID NO:7 have an amino acid sequence selected from the group consisting of HG, GR, RG and AR, (ii) said VL CDR2 has the sequence of SEQ ID NO:11, (iii) said VL CDR3 has the sequence of SEQ ID NO:12, (iv) said VH CDR1 has the sequence of SEQ ID NO:13, (v) said VH CDR2 has the sequence of SEQ ID NO:14, and (vi) said VH CDR3 has the sequence of SEQ ID NO:16, wherein positions 8-10 of SEQ ID NO:16 have an amino acid sequence selected from the group consisting of THW, YNW, TTW and STY, and, (b) a therapeutic moiety, wherein, following said contacting, said therapeutic moiety inhibits growth of said cell.

28. A method of claim 27, further wherein said VL CDR1 has the sequence of SEQ ID NO:7 and said VH CDR3 has the sequence of SEQ ID NO:16.

29. A method of claim 27, wherein said VL chain has the sequence of SEQ ID NO:20 and said VH chain has the sequence of SEQ ID NO:21, except that, optionally, said VL chain has a cysteine in place of glycine at position 100 and said VH chain has a cysteine in place of arginine at position 44, as these positions are numbered according to the "Kabat Numbering".

30. A method of claim 27, wherein said antibody is selected from the group consisting of an scFv, a dsFv, a Fab, or a $F(ab')_2$.

31. A method of claim 27, wherein said therapeutic moiety is selected from the group consisting of a cytotoxin, a drug, a radioisotope, or a liposome loaded with a drug or a cytotoxin.

32. A method of claim 31, wherein the therapeutic moiety is a cytotoxin selected from the group consisting of ricin A, abrin, ribotoxin, ribonuclease, saporin, calicheamycin, a mutated diphtheria toxin, a mutated *Pseudomonas* exotoxin A ("PE"), and botulinum toxins A through F.

33. A method of claim 32, wherein said mutated PE has the amino acid sequence of SEQ ID NO:22.

34. A method of claim 32, wherein said mutated PE has the amino acid sequence of SEQ ID NO:23.

35. A method for detecting the presence of a CD22+ cancer cell in a biological sample, said method comprising:

(a) contacting cells of said biological sample with the antibody of claim 17

(b) washing said cells to remove unbound antibody, and (c) detecting the presence or absence of bound antibody, wherein detecting the presence of said antibody indicates the presence of a CD22+ cancer cell in said sample.

36. A method of claim 35, further wherein said VL CDR1 has the sequence of SEQ ID NO:7 and said VH CDR3 has the sequence of SEQ ID NO:16.

37. A method of claim 35, further wherein said antibody is attached to a detectable label.

38. A kit for detecting the presence of a CD22+ cancer cell in a biological sample, said kit comprising:

(a) a container, and (b) an antibody that binds to CD22, said anti-CD22 antibody has a variable light (VL) chain comprising three complementarity determining regions (CDRs), and a variable heavy (VH) chain comprising three CDRs, further wherein (i) said VL chain CDR1 has the sequence of SEQ ID NO:7, wherein positions 4-5 of SEQ ID NO:7 have an amino acid sequence selected from the group consisting of HG, GR, RG and AR, (ii) said VL CDR2 has the sequence of SEQ ID NO:11, (iii) said VL CDR3 has the sequence of SEQ ID NO:12, (iv) said VH CDR1 has the sequence of SEQ ID NO:13, (v) said VH CDR2 has the sequence of SEQ ID NO:14, and (vi) said VH CDR3 has the sequence of SEQ ID NO:16, wherein positions 8-10 of SEQ ID NO:16 have an amino acid sequence selected from the group consisting of THW, YNW, TTW and STY.

39. A kit of claim 38, further wherein said VL CDR1 has the sequence of SEQ ID NO:7 and said VH CDR3 has the sequence of SEQ ID NO:16.

40. A kit of claim 38, further wherein said antibody is fused or conjugated to a detectable label.

* * * * *